United States Patent [19]

Fowler et al.

[11] 3,958,078

[45] May 18, 1976

[54] X-RAY INSPECTION METHOD AND APPARATUS

[75] Inventors: Robert Z. Fowler; Bruno W. Hautaniemi, both of Ithaca; Edgar W. Seymour, Freeville; Hans G. Jorgensen, Ithaca, all of N.Y.

[73] Assignee: Ithaco, Inc., Ithaca, N.Y.

[22] Filed: Aug. 30, 1974

[21] Appl. No.: 502,083

[52] U.S. Cl. .................................. 178/6.8; 178/6; 178/DIG. 1; 178/DIG. 5; 178/DIG. 36; 178/DIG. 37; 178/DIG. 38; 178/7.2; 250/359; 250/360; 250/358 R
[51] Int. Cl.$^2$.......................................... H04N 7/18
[58] Field of Search.................. 178/6, 6.8, DIG. 37, 178/DIG. 1, DIG. 5, 7.2, DIG. 36, DIG. 38; 250/358–360

[56] References Cited
UNITED STATES PATENTS

| | | | |
|---|---|---|---|
| 2,532,644 | 12/1950 | Robinson | 250/52 |
| 2,995,728 | 8/1961 | Jacobs | 340/149 |
| 3,384,235 | 5/1968 | Schulze | 209/73 |
| 3,580,997 | 5/1971 | Webb | 178/6.8 |
| 3,603,729 | 9/1971 | Sperber | 178/6.8 |
| 3,729,632 | 4/1973 | Cho | 250/83.3 D |
| 3,746,784 | 8/1971 | Van Oosterhout | 178/6.8 |
| 3,768,645 | 10/1973 | Conway | 209/111.5 |
| 3,769,507 | 10/1973 | Kenney | 250/52 |
| 3,777,169 | 12/1973 | Walter | 178/6 |
| 3,849,650 | 11/1974 | Patten | 250/321 |

*Primary Examiner*—Robert L. Griffin
*Assistant Examiner*—Edward L. Coles
*Attorney, Agent, or Firm*—Richard G. Stephens

[57] ABSTRACT

Articles such as glass jars filled with food products are inspected for defects by scanning an x-ray image to provide video signals which are processed in a novel manner to provide increased sensitivity to detect very small foreign particles without decreasing a tolerance for normal variations, to inspect substantially the entire contents of a container such as a jar even if it has a varying diameter, without the need for precise positioning of the articles within an inspection zone, and without a need for an x-ray or optical mask tailored to fit each type of jar to be inspected.

51 Claims, 29 Drawing Figures

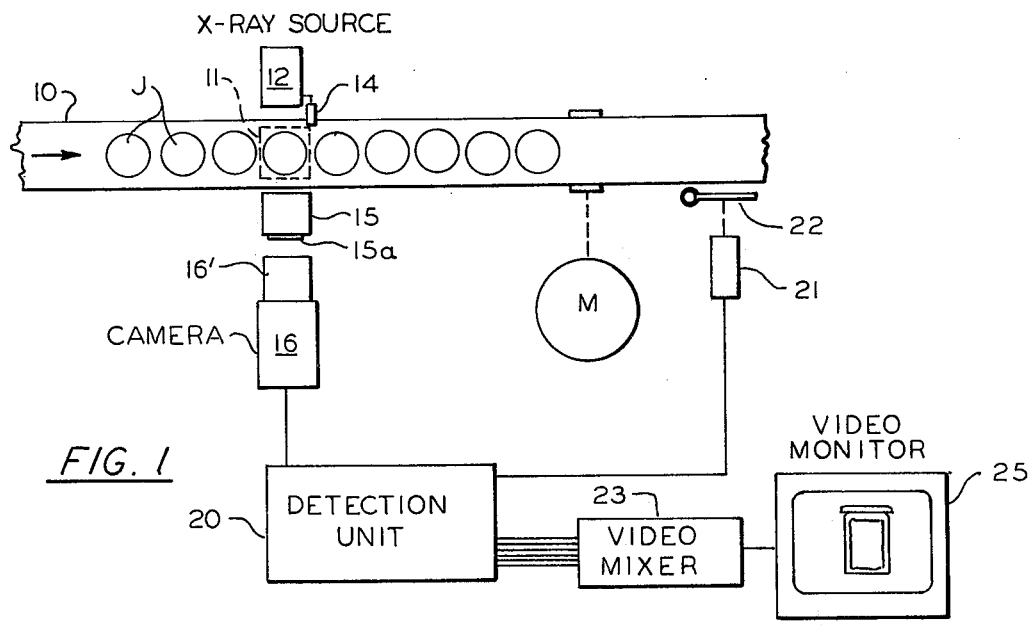
FIG. 1
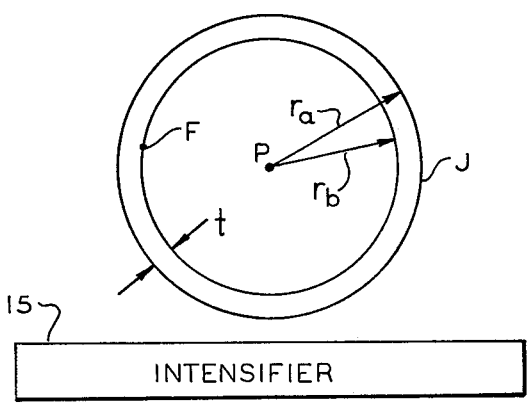
FIG. 2a
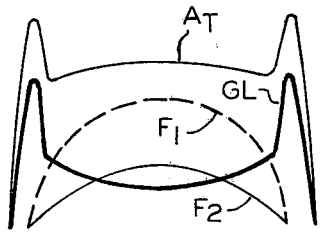
FIG. 2b
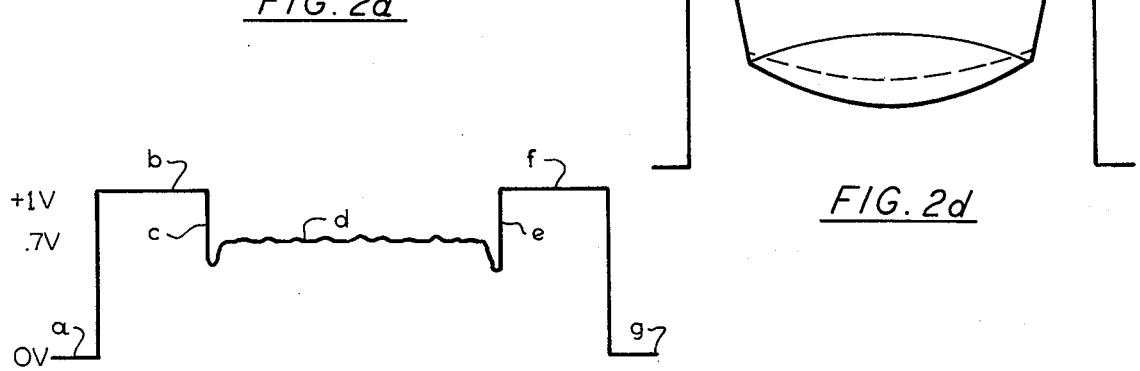
FIG. 2c
FIG. 2d

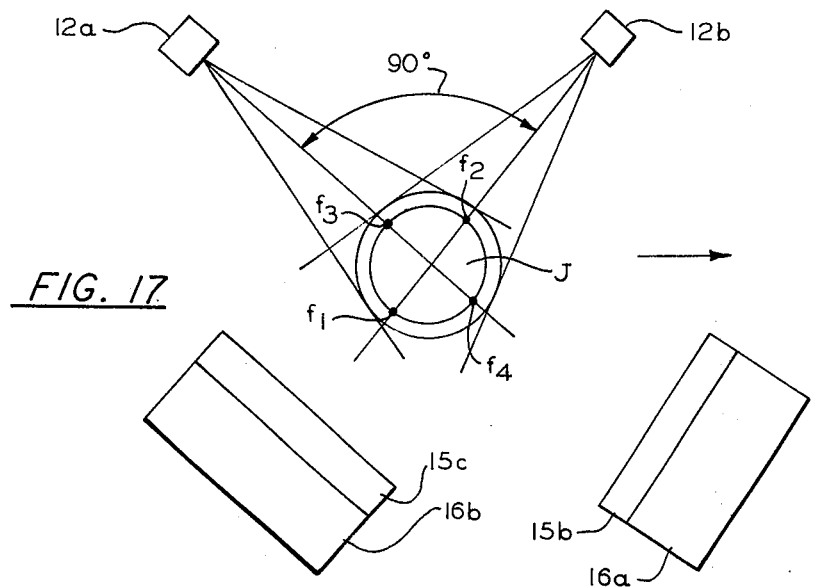
FIG. 17
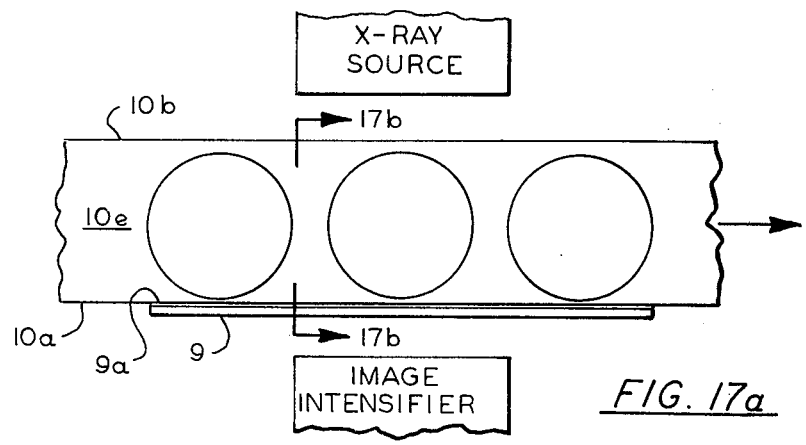
FIG. 17a
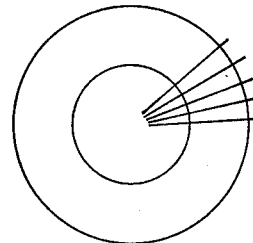
FIG. 17b
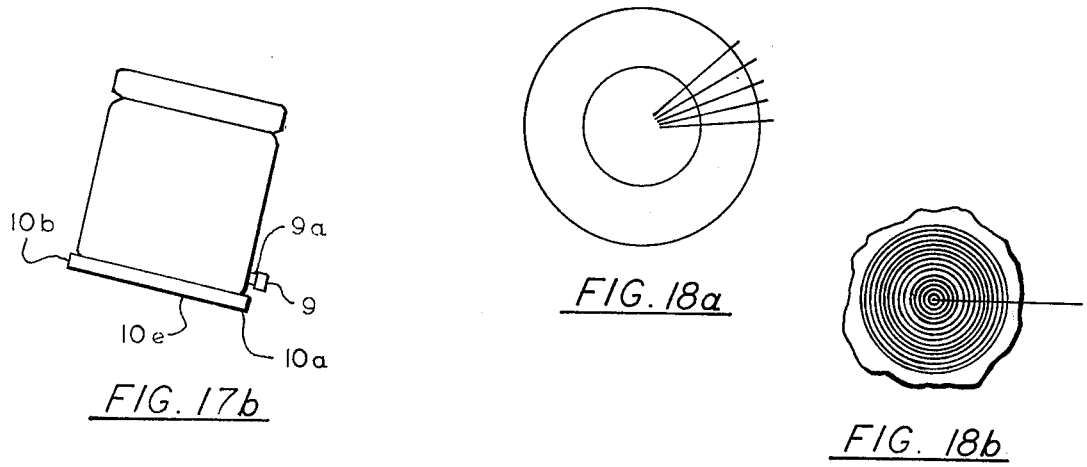
FIG. 18a
FIG. 18b

X-RAY INSPECTION METHOD AND APPARATUS

This invention relates to x-ray inspection method and apparatus, and more particularly, to improved method and apparatus for detecting the presence of foreign particles in various packaged articles such as glass bottles or jars of food, or metal cans containing foods or beverages, although it will become apparent as the description proceeds that the invention also may be used in connection with the inspection of various other articles. The invention is particularly intended for use in food processing plants or the like where it is desired that large quantities of articles such as jars of foods be checked rapidly in succession, as they are transported along a conveyor, for example.

Various prior systems proposed for the same or similar purposes have contemplated irradiating an article to be tested with x-ray radiation, detecting the radiation which has passed through the article by a transducer which provides electrical signals commensurate with the radiographic density of portions of the article, and then processing the electrical signals to detect foreign particles or defects in the article. Some such systems are not satisfactory for rapid and thorough inspection of moving articles carried on a conveyor because they only measure the radiographic density of portions of the articles, and allow foreign particles or defects in other portions of the articles to pass undetected. One object of the present invention of to provide improved x-ray inspection method and apparatus which will allow the entire contents of a package to be rapidly and thoroughly checked.

Where articles or a product to be inspected are carried in containers such as glass bottles or jars, it is necessary that a useful inspection system ignore the walls, bottom and cap of a normal glass jar and not allow their detection to cause a reject indication. On the other hand, it is vitally necessary that the existence of any foreign glass particle inside such a jar be detected, even if such a particle is lying closely adjacent a wall or the bottom of the jar. The need to reliably discriminate between normal jar structure and foreign objects such as glass particles greatly complicates the problem of effective inspection. Some prior systems provide inspection of portions of an article by applying the radiation which passes through the article to an image intensifier, by scanning the output image field from the intensifier by means of a television camera, and processing the video signals from the TV camera. Various prior systems of this general nature have been disadvantageous because they have been complex and expensive. To prevent article containers such as normal jar walls and the like from being detected as defects, some prior systems have required the use of special x-ray masks with which the articles must be precisely aligned when they are irradiated, making such systems either unsuitable for use with conveyor-transported articles, or requiring very precise positioning of the article on the conveyor and requiring that very precise time relationships be maintained between conveyor movement and the operation of timing circuits which process the television camera video output signal. To prevent normal jar structure from being erroneously detected as a defect, some prior systems have utilized optical masks which limit the field viewed by the television camera. These systems also require precise registration. As well as imposing stringent registration and timing problems, systems dependent upon the use of masks are also disadvantageous in that different types of masks must be made and stocked and installed in order to inspect articles having different shapes. One object of the present invention is to provide an improved x-ray inspection method and apparatus which does not require the use of x-ray masks or optical masks, nor require precise control of conveyor speed, nor require precise positioning of articles on coneyor.

Various prior systems which have been proposed dispense with the use of x-ray or optical masks and instead blank the television camera, or disable certain detection logic circuits, so that the container walls and the like will not be falsely registered as foreign particles. The prior systems of this type of which we are aware are disadvantageous in that they are unable to effectively inspect the entire contents of a jar or bottle. While it is simple to provide camera blanking or logic circuit disabling during two predetermined portions of each scan line across an image of a jar, so that image portions corresponding to the two side walls of a jar will be ignored, such an arrangement tends to be useful only with jars having a uniform diameter. If a jar has a varying diameter such systems must be adjusted so as to inspect an area of slightly less width than the minimum diameter, so that large portions of the contents of such a jar may remain uninspected. An important object of the present invention is to provide improved x-ray inspection method and apparatus which will allow substantially all of the contents of a jar to be reliably inspected, without falsely detecting the wall structure of the jar, even though the jar may have a varying diameter. It is perhaps possible to provide extremely complex blanking circuits tailored in accordance with the geometry of a particular jar which would blank a camera or disable detection logic in a variable manner for that particular jar, but such circuits would be extremely complex and expensive, and useful for only a jar of one size and shape. Another object of the present invention is to provide improved x-ray inspection method and apparatus which is useful with jars of numerous sizes and shapes.

A number of prior art x-ray inspection systems are disadvantageous because they allow various small foreign particles or defects to pass undetected. Some prior systems provide television scanning of an entire x-ray image of an article, analog integration of the scanning-derived signals throughout the scanning field, and means for rejecting the article if the integrator output at the conclusion of the scanning field exceeds a predetermined upper limit or falls below a predetermined lower limit. Normal articles having no foreign particles or defects may have some appreciable difference in radiographic density, and in order to avoid the rejection of such articles, the upper and lower limits must be substantially apart from each other, to provide a substantial tolerance for normal variation in radiographic density. However, the presence of a small foreign particle causes a small change in the total or integrated radiographic density, and if the percentage change caused by the foreign particle is less than the tolerance required for normal variation, the foreign particle passes wholly undetected. To increase the ability of such systems to detect small foreign particles, some prior systems have divided the x-ray image field into plural zones, with each zone being covered by a separate group of television camera scan lines. Then, by separately integrating the scan signals for each zone, smaller foreign particles can be detected without decreasing the tolerance for normal variations, since a foreign particle of a given size then will cause a larger percentage change in the integrator output signal. The greater the number of zones the field is divided into, the greater becomes the ability of the system to detect very small particles, but the use of more zones ordinarily disadvantageously requires the provision of more equipment and may require increased operating time. Theoretically, this technique could be extended, sometimes with the disadvantages of great cost and complexity, so that each scan line comprised a separate zone, and while that would result in a further increase in the ability to detect abnormalities, the system would still be insufficiently sensitive to detect some minute abnormalities. One very important object of the invention is to provide improved x-ray inspection method and apparatus having a greater ability to detect very minute abnormalities in articles without having to decrease the tolerance for normal variations.

A variety of articles which it is desirable to inspect may include not only foreign particles, such as bits of glass, metal or bone, for example, having high radiographic density, but also voids or air pockets, or pieces of fat having a lower radiographic density than the other contents of the article container. Prior art systems which integrate the video signals over appreciable zones are disadvantageous because the presence of a first foreign particle or a void having a low density which is located in the same zone as a second foreign particle of high density can offset or cancel the change in integrator output which either foreign particle otherwise would cause, thereby causing both of the foreign particles to pass undetected. Another object of the present invention is to provide x-ray inspection method and apparatus wherein the presence of foreign particles having one density will not mask the presence of foreign particles having a different density, i.e., so that abnormalities of opposite sense may not cancel each other so as to prevent their detection.

Prior art systems which integrate video signals commensurate with radiographic density are also disadvantageous in that the instantaneous magnitude of the video signal which is integrated, and hence also the final integrated value which is used for rejection or classification, are very dependent upon both the intensity of the x-ray beam provided by the x-ray source and the gain of the camera tube, both of which factors are difficult to maintain at constant predetermined levels. Another important object of the invention is to provide improved x-ray inspection method and apparatus wherein the reliability of detection or classification is made substantially less dependent upon x-ray source intensity and camera tube gain.

Detection of minute particles requires that a camera operate with substantial sensitivity, and some television cameras have slight irregularities or imperfections in their target screen which result in brief reductions in the camera output signal when the scanning beam crosses a target area having a slight imperfection. It is necessary that the irregularities in the video signal caused by such target imperfections not be interpreted as foreign particles in the food products. In accordance with a further aspect of the present invention, means are provided to briefly prevent detection of a defect when the camera tube scans a portion of its screen having an imperfection. This allows one to use "imperfect", and hence much less expensive camera tubes for foreign particle inspection, which is another object of the present invention.

In numerous applications it is advantageous if articles to be inspected need not be precisely positioned on a conveyor or the like to insure a precise spacing between successive articles. One object of the present invention is to provide an improved inspection system in which such spacing need not be precisely controlled. For example, if when a given jar is being inspected, a preceding and/or a following jar happens to extend partially into the inspection zone, it is desirable that its presence not affect inspection of the jar then intended to be inspected, and provision of method and apparatus which operate in such a desired fashion is another object of the invention.

It has been known in prior scanning-type x-ray inspection systems to enable a detection logic circuit a first predetermined time after an edge has been detected, and to maintain the detection logic circuit enabled for a second predetermined time while the inside contents of the jar are being inspected. This has been done by using a pair of cascaded pulsers, the first of which is set by an edge detector and provided with a period corresponding to the width of the glass on the leading wall of the jar. The second pulser was triggered by the reset of the first, and flaw detection allowed to take place while the second pulser was set. A problem occurred in that the period of the second pulser arbitrarily had to be shortened so that inspection was terminated before the trailing edge glass wall portion of the image was scanned. If the jar had a varying diameter, the period of the second pulser had to be short enough to cut off detection so as to prevent a false indication for a scan line across the minimum inside diameter portion of the jar, which resulted in no detection of product inside wider portions of the jar. Detection could not be terminated by sensing the trailing wall of the jar, since the sensing of the trailing edge would itself register a defect. In other words, to prevent the trailing edge from registering a defect, one was seemingly confronted with the problem of predicting that the trailing edge was about to be encountered and disabling the detection logic just before that edge was in fact encountered. Since the distance of the trailing edge from the leading edge varies appreciably in jars of varying diameter, the problem appeared to be rather formidable. However, in accordance with the present invention, the problem is overcome in an extremely simple and inexpensive manner by merely delaying video comparison for a predetermined time. The video signal from the camera is applied to the comparison circuitry with a predetermined delay, and the detection logic responsive to the comparison circuitry outputs is enabled and disabled with that predetermined delay taken into account. Thus as a scan line crosses a jar, the detection logic is enabled at a time after the leading edge of the jar is intercepted which is equal to or slightly more than the time required to scan through the glass side wall of the jar plus the amount which the video signal has been delayed, and then later disabled at a time after the inside edge of the trailing side wall of the jar is intercepted equal to or slightly less than the amount which the video signal has been delayed.

Other objects of the invention will in part be obvious and will in part appear hereinafter.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

For a fuller understanding of the nature and objects of the invention reference should be had to the following detailed description taken in connection with the accompanying drawings, in which:

FIG. 1 is a schematic diagram largely in block form illustrating a jar inspection system of which the present invention is a part.

FIG. 2a is a plan view diagram of a food jar upon which x-rays are projected.

FIG. 2b contains graphs showing typical variations in radiographic absorption across a food jar.

FIG. 2c illustrates a typical waveform derived as a camera scans a radiographic image of a glass jar of food.

FIG. 2d is a waveform diagram illustrating several types of waveforms obtained by scanning images of several types of food jars.

Figure 3A:
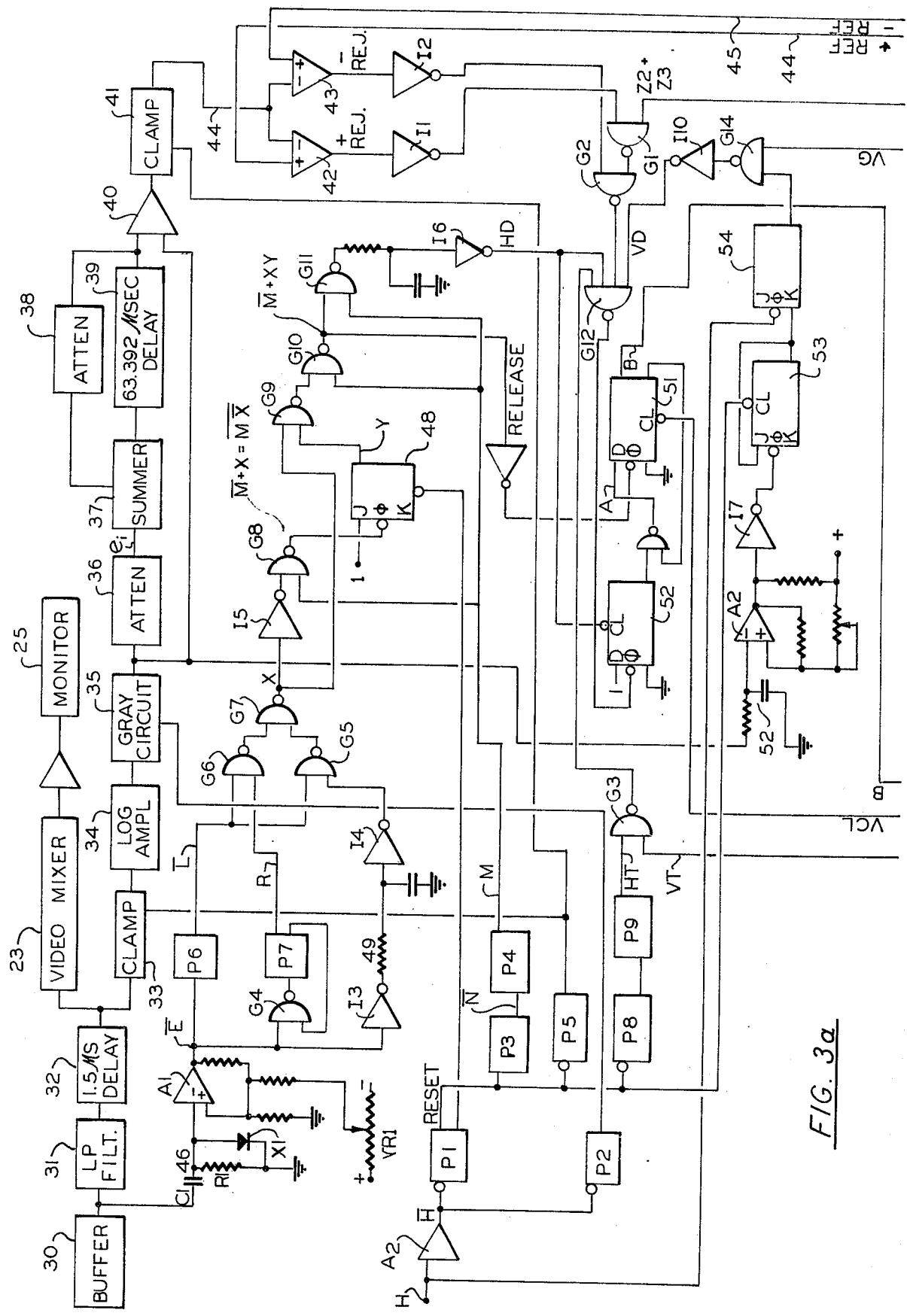
Figure 3B:
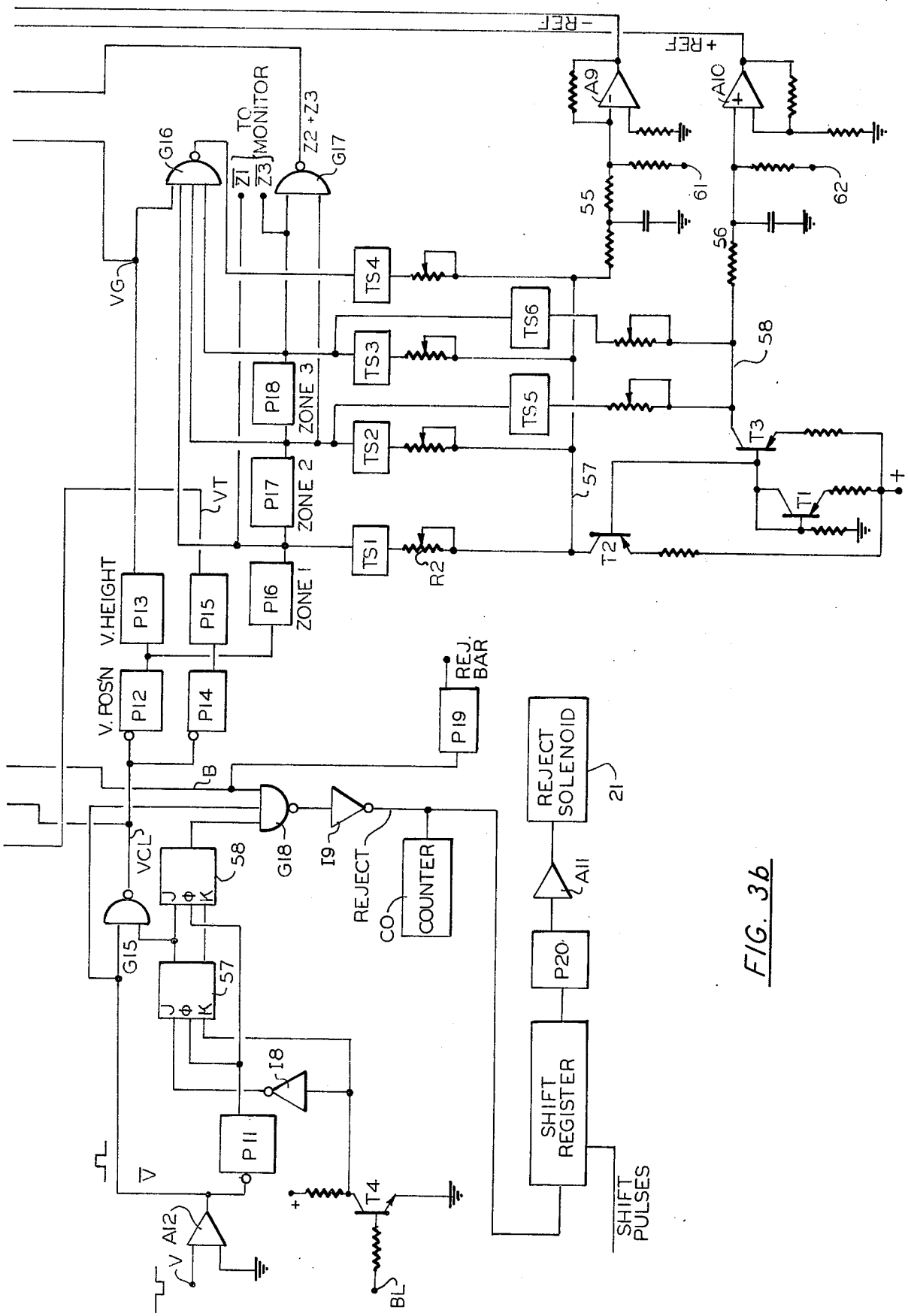

FIGS. 3a and 3b together comprise a schematic diagram illustrating one form of detection unit constructed in accordance with the present invention.

Figure 4:
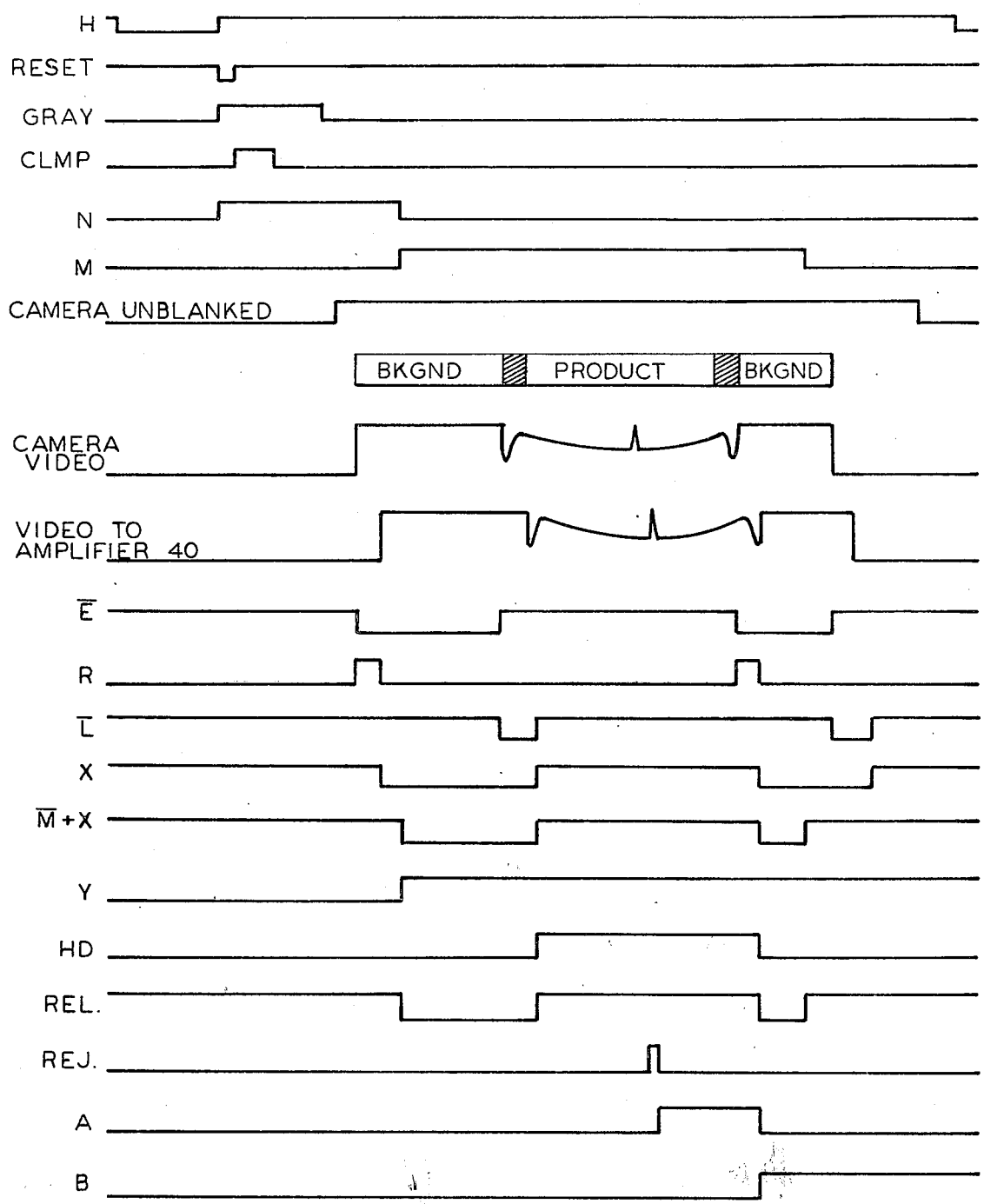
Figure 5:
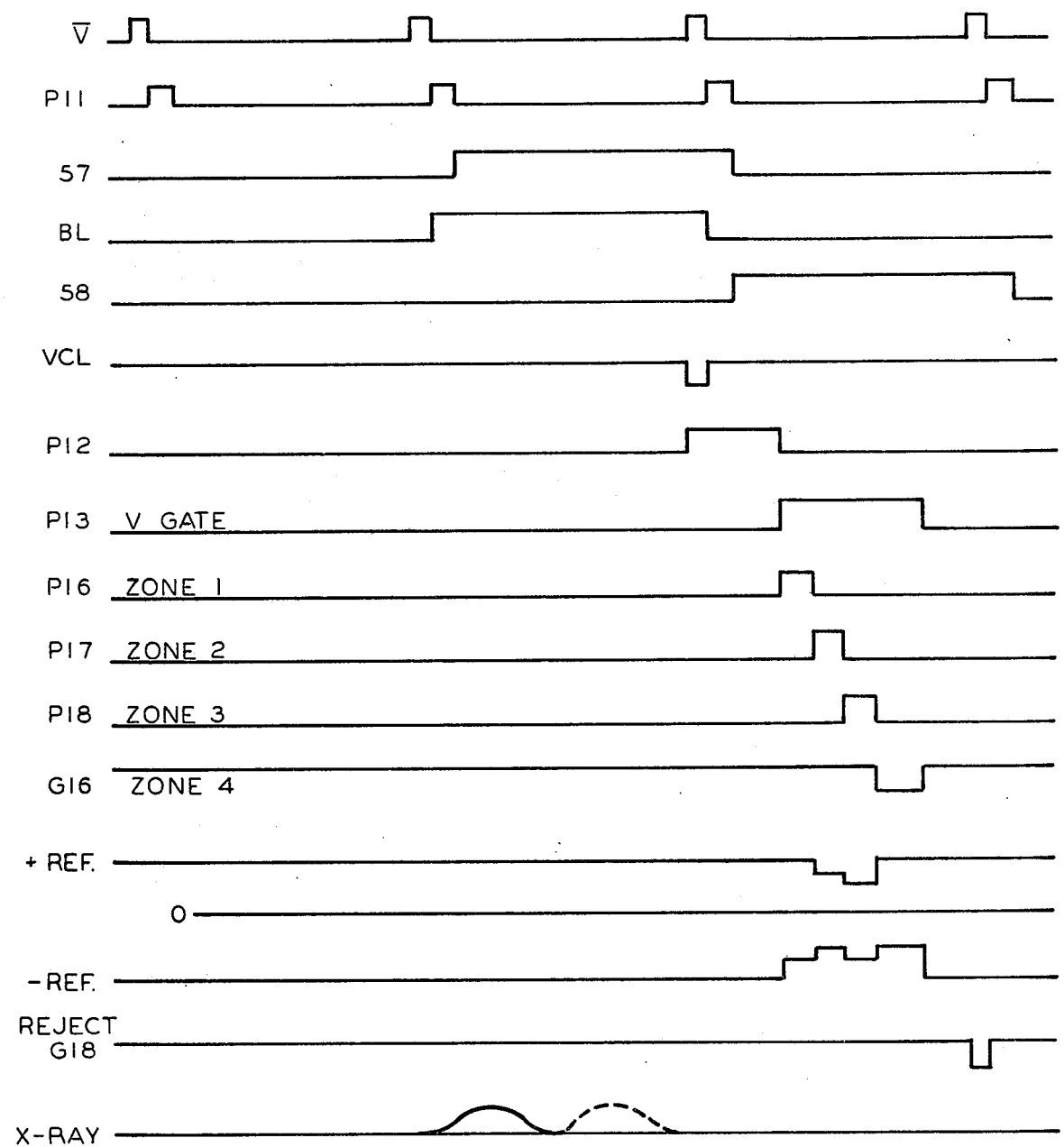

FIGS. 4 and 5 are a series of waveforms forming timing diagrams useful for understanding the horizontal sweep timing and vertical sweep timing, respectively.

Figure 6:
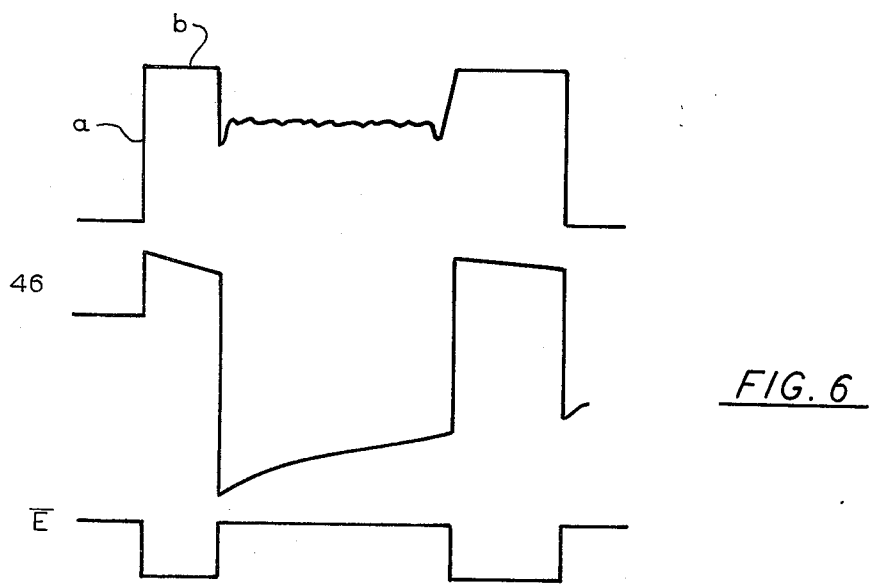

FIG. 6 is a group of waveforms useful in understanding the operation of an edge detector portion of the invention.

Figure 7:
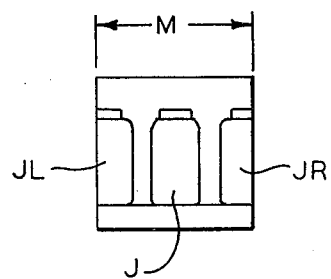

FIG. 7 is a diagram useful in understanding how the invention is capable of ignoring partially scanned jars.

Figure 8:
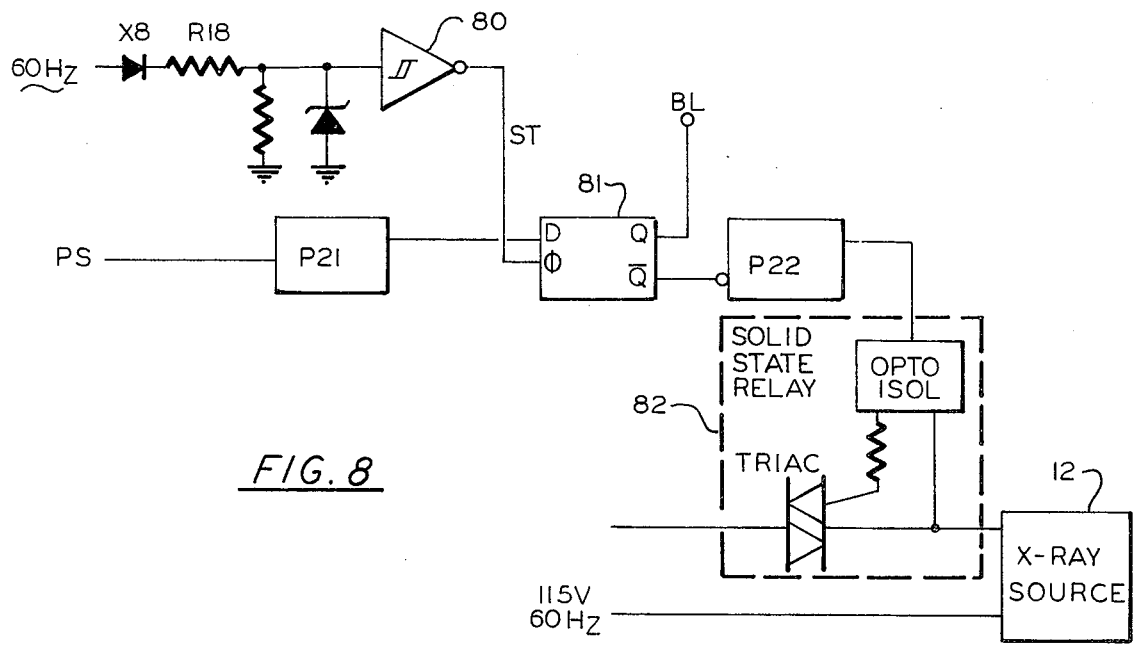
Figure 8A:
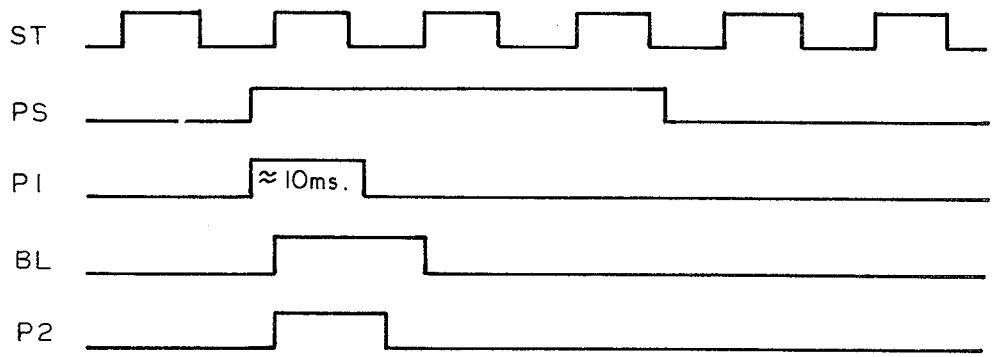

FIG. 8 is a schematic diagram illustrating an exemplary control system for synchronizing the camera with the x-ray source, and FIG. 8a is a timing diagram useful for understanding the operation of the system of FIG. 8.

Figure 8B:
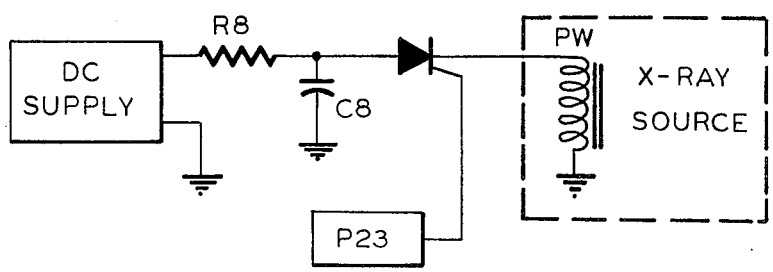

FIG. 8b is a diagram illustrating one exemplary manner in which the x-ray source may be appropriately powered from a DC power supply.

Figure 9:
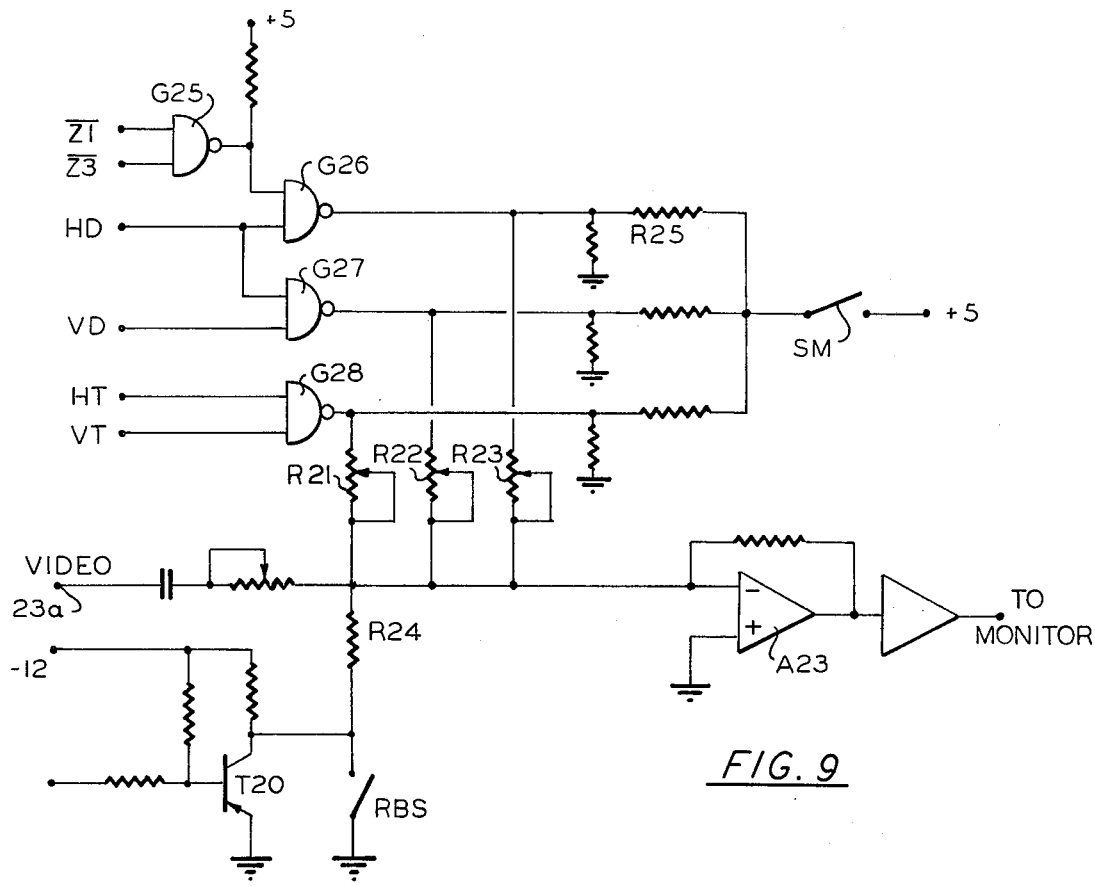

FIG. 9 is a schematic diagram of an exemplary form of video mixer circuit which may be used to provide indicia on a television monitor in connection with the invention.

Figure 10:
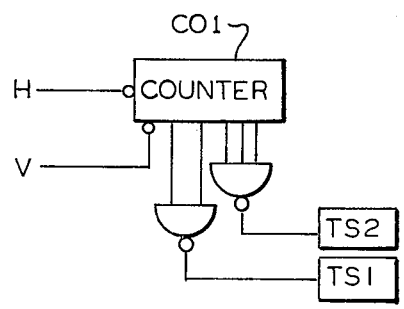

FIG. 10 is a schematic diagram partially illustrating one modification which may be made to a reference voltage generating portion of FIG. 3b.

Figure 11:
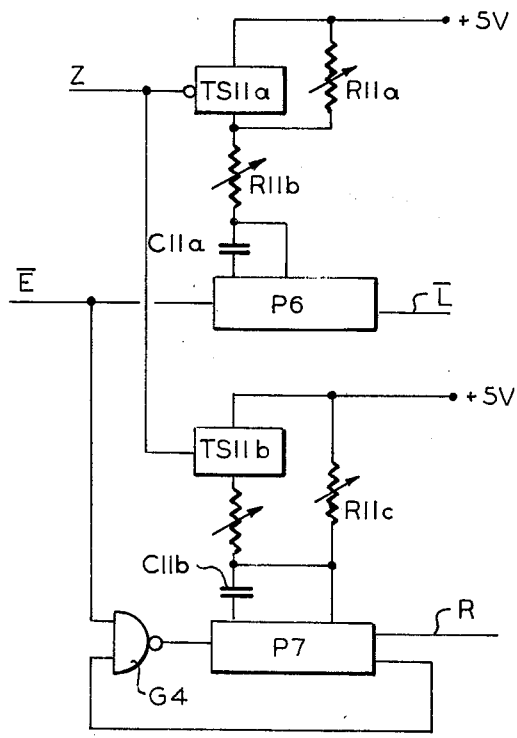

FIG. 11 is a schematic diagram illustrating a modification which may be made to a portion of FIG. 3a.

Figure 12:
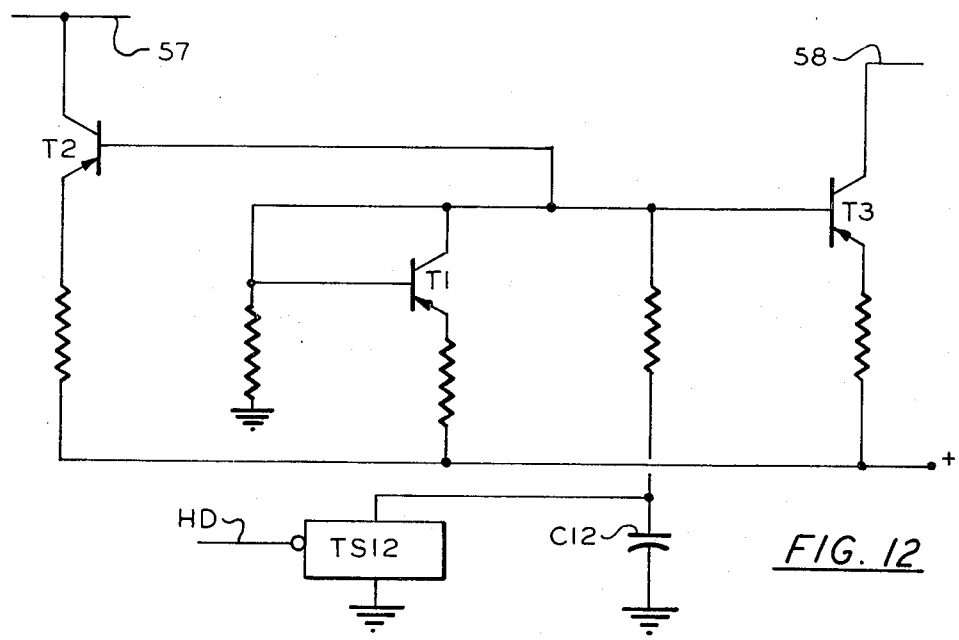

FIG. 12 illustrates a further modification which may be made to FIG. 3b to automatically vary detection sensitivity during a portion of each scan line.

Figure 13:
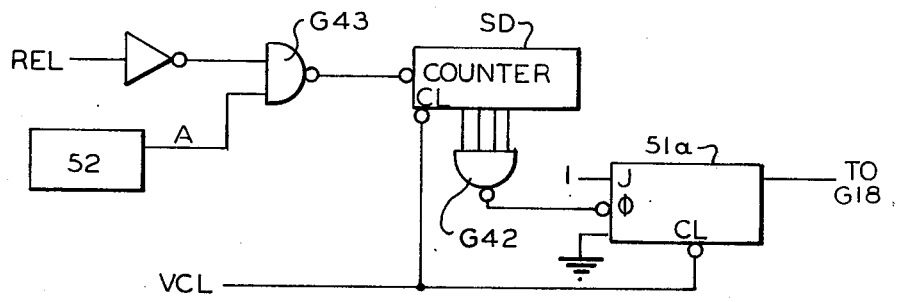

FIG. 13 illustrates a modification which may be made to the system of FIGS. 3a and 3b to provide rejection signals only if foreign particles or defects are detected in plural scan lines.

Figure 14:
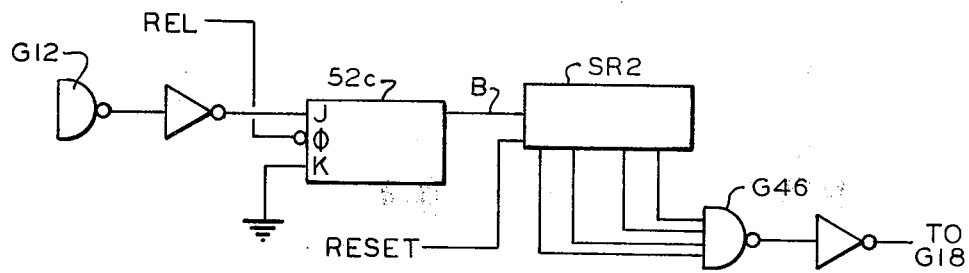

FIG. 14 illustrates a modification which may be made to the systems of FIGS. 3a and 3b to provide rejection signals only if defects are detected in plural successive scan lines.

Figure 15:
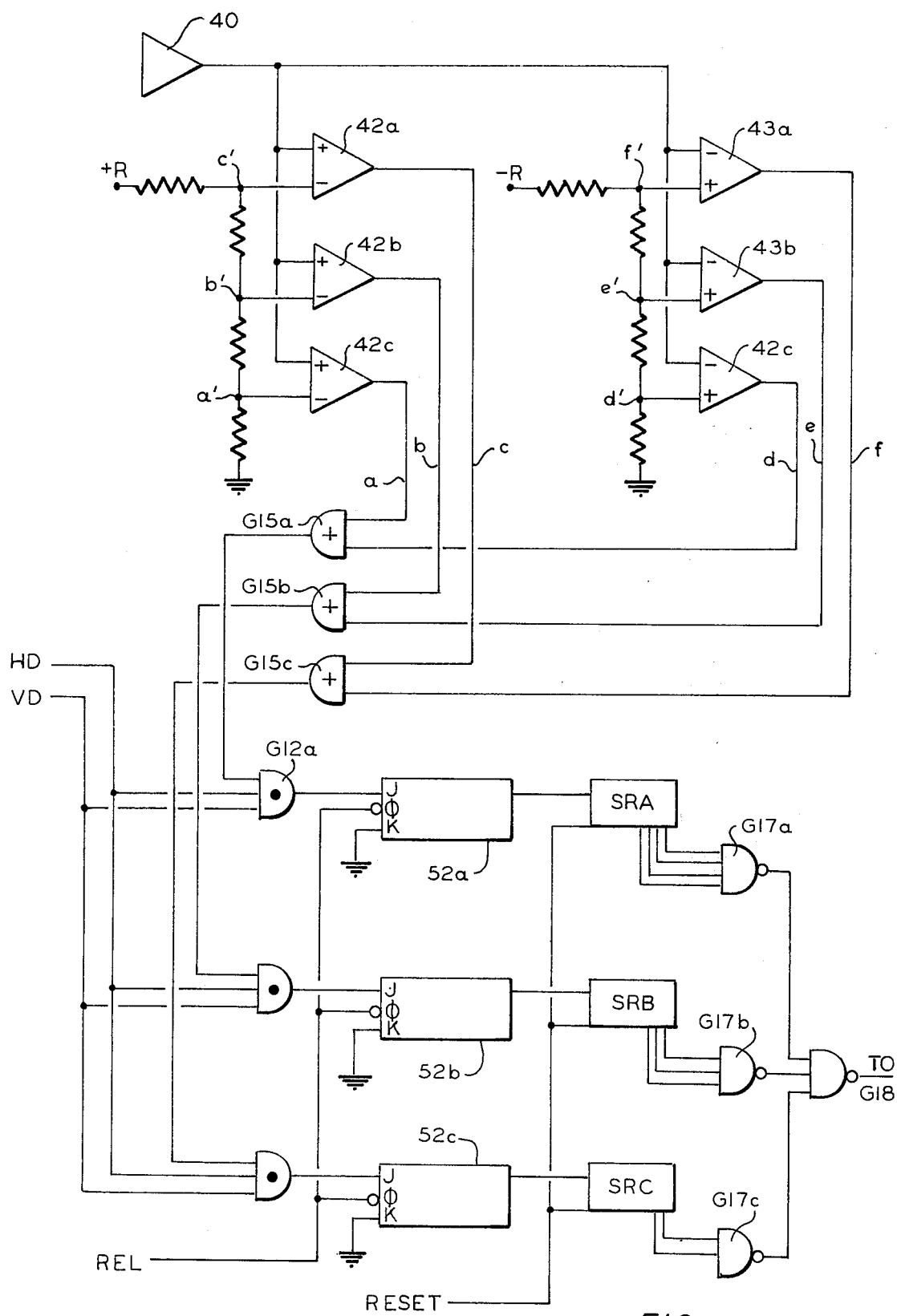

FIg. 15 illustrates a modification which may be made to the system of FIGS. 3a and 3b to provide rejection based on criteria which vary in accordance with the magnitudes of changes in density within various ranges, and the number of such changes in each range.

Figure 16:
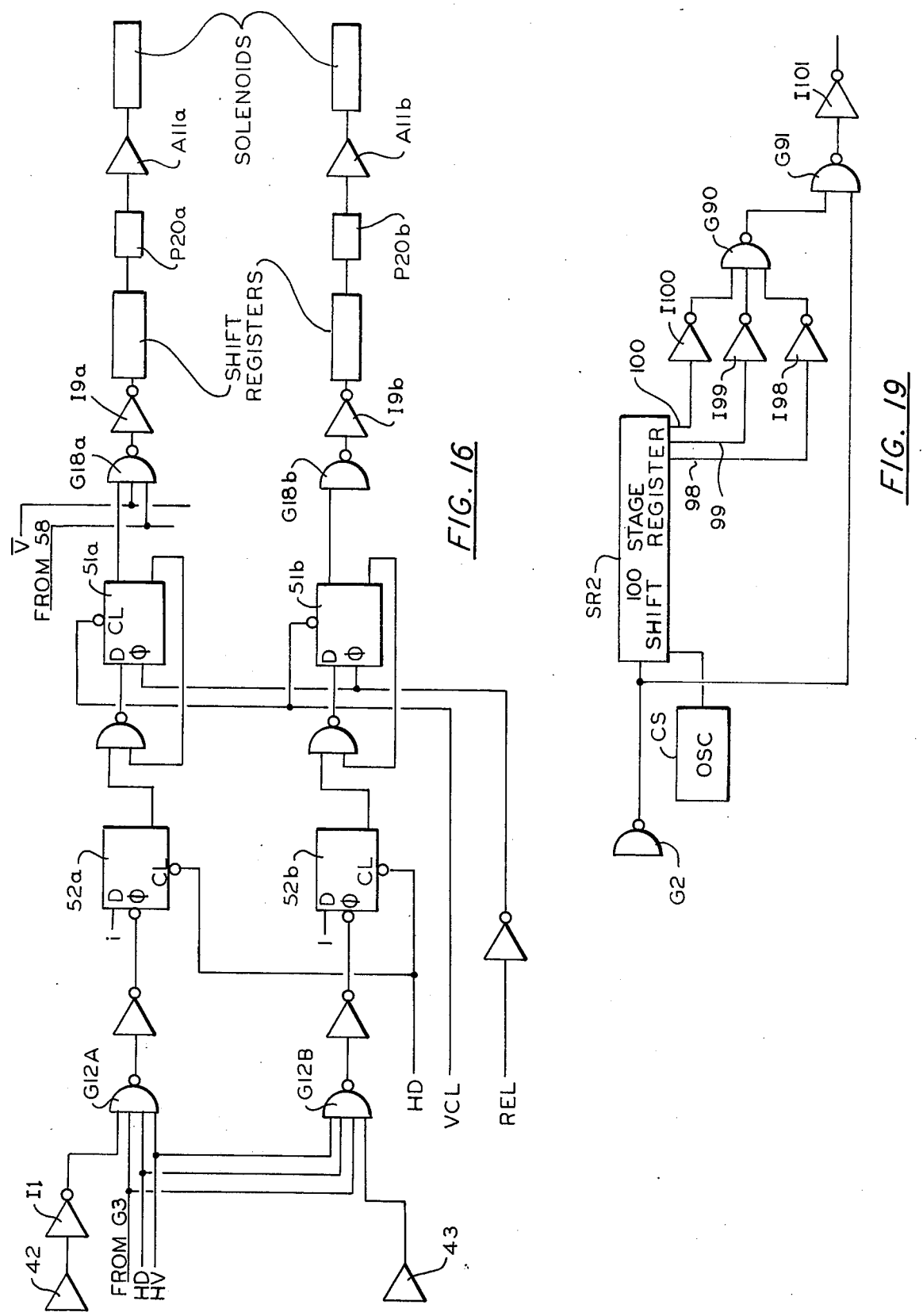

FIG. 16 illustrates a modification which may be made to the system of FIGS. 3a and 3b to provide separate indication, and separate classification, if desired, of articles which have differing types of detected defects.

FIG. 17 is a geometrical block diagram illustrating an alternate embodiment in which plural beams of x-rays are passed through each article, in differing directions.

FIGS. 17a and 17b are plan and end view diagrams, respectively, illustrating one manner in which articles such as jars may be rotated in between plural x-ray exposures.

FIGS. 18a and 18b are geometrical diagrams illustrating two alternate scanning patterns which may be utilized.

FIG. 19 is a schematic diagram illustrating a modification which may be made to the system of FIGS. 3a and 3b to provide rejection only if defects are detected at corresponding points along successive scan lines.

In FIG. 1 articles J,J. assumed to be glass jars of generally-cylindrical shape filled with a food product are transported by means of conveyor 10 past an inspection zone (shown in dashed lines at 11) at which is located a conventional x-ray source 12. Conveyor 10 is shown driven by a conventional motor M, which may be, for example, a squirrel-cage induction motor, a synchronous induction motor, or any one of a variety of DC motors. The speed of conveyor 10 need not be precisely controlled, since, as will be seen below, inspection of a given jar requires that it be exposed to x-ray radiation for only a very brief interval, less than 1/120th of a second, and because no masks need be provided, the articles need not be precisely registered with a mask or the like during the brief instants when they are irradiated. As each jar arrives at inspection zone 11, its presence is sensed by conventional presence-sensing means 14, which may comprise a photo-sensor, a magnetic sensor, a mechanical sensor, or even various types of proximity sensors, such as those which indicate article presence by detuning or loading a radio frequency circuit. The sensor may be operated by detection of the leading edge of each jar, for example, or by detecting the presence of a metal cap on a bottle, or, in cases where jar positions are fairly accurately determined by conveyor position, by sensing conveyor movement or the presence of conventional article carriers (not shown) which may be used to carry some types of articles along the conveyor. As the presence sensor 14 detects the presence of a jar at the inspection zone, it applies a signal to x-ray source 12, briefly energizing source 12 so that a beam of x-ray radiation is directed toward the jar then situated in the inspection zone. The beam of radiation is shaped and directed by conventional means so that it encompasses the entire profile of the jar, plus some surrounding area, and where articles are conveyor-transported, the beam may also strike a portion of the conveyor beneath the jar located at the inspection zone. In systems where jars of various different sizes are to be inspected, the x-ray beam is made to exceed in cross-section the profile of the largest jar to be inspected.

A conventional x-ray image intensifier 15 is shown located on the opposite side of the conveyor from source 12. It will be understood that radiation which is not intercepted by a jar will reach the image intensifier without substantial decrease in intensity, while radiation which is intercepted by the jar and/or the contents of the jar will be attenuated in accordance with the radiographic absorption of the jar and/or contents, and that a radiogram image characteristic of jar and its contents will appear on the output screen 15a of image intensifier 15. The image on screen 15a is viewed by a conventional camera tube 16, which includes a conventional scanning beam and conventional deflection and blanking circuits not shown in FIG. 1. An RCA Type 4532A silicon diode array camera has proven satisfactory. The beam of camera 16 is blanked or cut off during the interval the x-ray source is energized, but during that interval the image on screen 15a of the image intensifier causes a charge characteristic of the image to be stored on the target of camera 16. In one successful embodiment of the invention the x-ray source was energized for approximately 1/120th of a second. The x-ray source may be completely conventional, and may comprise, for example, a source of the type widely used in dental x-ray equipment. The source may be energized by one-half-cycle of a conventional alternating-current 60 Hz source, for example, or may be energized by a DC pulse of desired duration. The camera 16 in FIG. 1 is assumed to view the image intensifier output screen 15a through a conventional optical lens 16'. The image can be transmitted from intensifier to camera through a fiber optics image coupler instead of, or in addition to a lens, of course. In some applications, such as where the portion of an article which one desires to inspect is considerably taller than it is wide, or vice versa, lens 16' may incorporate a conventional optical anamorphoser, of either the cylindrical lens or the prism type, to expand the narrow dimension of the image by a desired amount, so that the image covers a greater area of the camera target, thereby improving system resolution.

Shortly after the x-ray source is turned off, camera 16, is caused to scan its target for one field of scan lines, in conventional raster fashion, thereby providing a video signal. The video signal is applied to a detection unit 20, which includes many of the features of the present invention, and which will be described in detail. Detection unit 20 processes the video signal provided by camera 16 during that scanning field, providing a reject signal if various foreign particles or defects are detected by the processing of the video signal. The reject signal may be used to remove the jar from the conveyor, for example, and/or to actuate any of a variety of alarm, control, or indicator devices. The reject signal may be applied to a solenoid 21, so as to operate a conventional conveyor gate 22, for example, to remove a defective jar from the conveyor line. A scanning field during which the detection unit receives video signals from the camera may be termed an inspection scanning field. The camera 16 is preferably arranged then to scan its target for several more scan fields, without the camera video being processed by detection unit 20, such further scanning sensing to erase the image theretofore stored in the camera in preparation for receipt of a new image from the next jar to be inspected. As well as providing a reject signal to control removal of a defective jar from the conveyor line, detection unit 20 also applies output control signals to a video mixer circuit 23, which provides a video signal, suitably amplified at 24, to a conventional video monitor 25. Video signals are applied to monitor 25 during the scanning field during which detector unit 20 processes the camera video, together with marker signals which indicate the locations of areas which are inspected. By viewing the image of a jar in the inspection zone on the monitor, an operator is enabled to readily adjust the system to inspect jars of any size or shape which the system is designed to accommodate, and to verify that given defects will be detected by the system.

Figure 2:
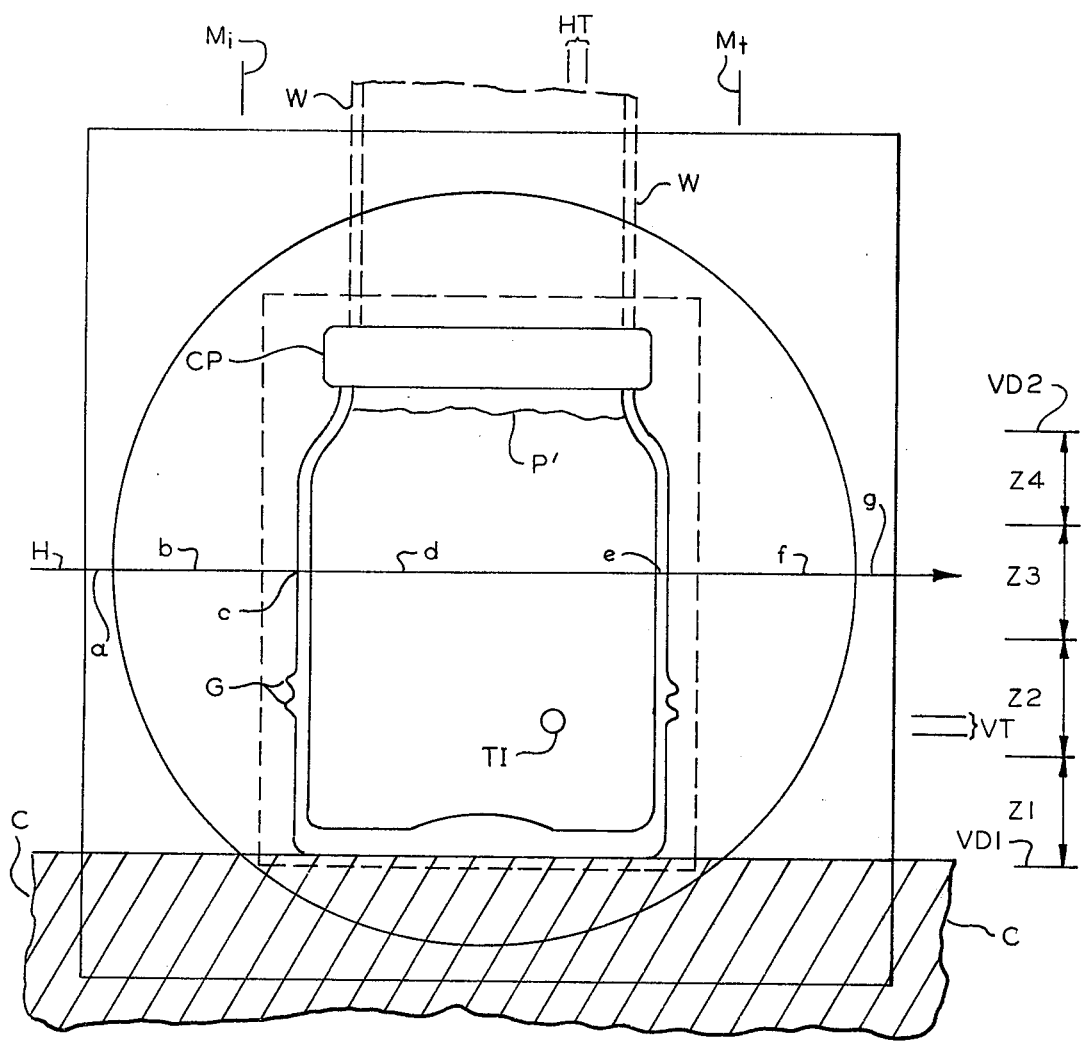
FIG. 2 is a diagram of an inspection field useful in understanding the operation of the invention.

When the x-ray source is pulsed and a radiograph image appears on the output screen of intensifier 15, the image which is stored in camera 16 comprises a circular image (assuming the intensifier output screen 15a is circular, which is by no means a requirement) having areas of diminished charge due to x-ray absorption by the jar and its contents, and an outer area of greater charge representing space surrounding the jar, which may be termed background. In FIG. 2 an image of a jar is shown within a circular area representing the bounds of the intensifier output image, and the solid line rectangle surrounding the circular represents the bounds of the camera scanning raster, i.e. the area covered by the camera beam when it is unblanked. While the raster area is shown in FIG. 2 as being larger than the circular area of the intensifier output image, it may instead be smaller, if desired, as is represented by the dashed-line rectangle in FIG. 2. In FIG. 2 a lower hatched area at C represents conveyor structure upon which the jar is supported. In some applications a jar or bottle may extend above the image and/or raster areas, as indicated by the dashed lines at W,W. The only requirement respecting the relationships between intensifier image size, raster size and bottle size is that the image and raster include a strip of background area along each side of the bottle, with each such strip having a length as great as the vertical dimension in which inspection is desired. In FIG. 2 the jar is assumed to contain a product up to a level indicated by a wavy line P', and assumed to carry a metal cap or cover CP. In FIG. 2 the jar is shown including a pair of circular ridges which extend around the jar. As successive scan lines across different portions of the zone containing such ridges, the detection sensitivity is desirably reduced, so that the variation in the video signals due to the changing glass thickness does not cause an erroneous rejection of a normal jar of food.

FIG. 2a is a plan view of a cross-section through a jar J assumed to contain a product P inside the jar, such as a cross-section taken at line H in FIG. 2, for example, X-rays $r_1$ to $r_5$ are projected from the source toward the jar. In FIG. 2a rays $r_1$ to $r_5$ are shown parallel to each other for sake of simplicity. In most applications the x-rays will emanate from a small area of the source in the form of a diverging beam, and hence not be precisely parallel. It will be seen that outside rays $r_1$ and $r_5$, which do not intercept the jar will pass to the intensifier with inappreciable attenuation. Rays $r_2$ and $r_4$ will be be seen to pass through thicknesses of glass appreciably greater than twice the wall thickness $t$ of the glass wall of the jar but through little or none of the food product, and central ray $r_3$ will pass through a thickness $2t$ of glass, and a substantial thickness of the food product P. If the wall of a jar has an outside radius (from the center of the jar) of $r_a$ and an inside radius $r_b$, so that the radial thickness $t$ of the jar wall is $r_a-r_b$, it can be shown that the glass thickness T through which the x-rays pass varies across the jar in accordance with the expression $$T = 2[(r_a^2 - x^2)^{1/2} - (r_b^2 - x^2)^{1/2}]$$

where $x$ is measured from the center of the jar, and that $dT/dx$, the rate of change of thickness across the jar, varies as $$(dT/dx) = 2x[(r_b^2 - x^2)^{-1/2} - (r_a^2 - x^2)^{-1/2}],$$

assuming, for each of the two expressions, that the rays are parallel. While recognizing that a central ray such as $r_3$ will pass successively through two walls of the jar, and that the wall of the jar may be of substantially uniform thickness, it is convenient in the description of the invention to refer to the jar portions of greater glass length through which rays such as $r_2$ and $r_4$ pass as the "side" walls of the jar. Inasmuch as the projected glass thickness in the general direction of the x-ray radiation varies continuously across the jar, generally in accordance with the first of the above expressions, it will be seen that what one chooses to consider the "width" of each side wall is somewhat arbitrary and will vary in different applications, depending not only upon the actual thickness $t$ of the glass, but also upon the absorption of the particular food product being inspected relative to that of the glass. Thus the two "side walls" of a glass jar may be considered to be those areas, at the extremities of the jar measured in a direction normal to the general direction of radiation, through which the amount of transmitted radiation cannot reliably be distinguished from foreign objects desired to be detected in the particular food product contained between the side walls. The x-ray absorption caused by the glass thus will tend to vary across the jar in the manner generally indicated by curve GL in FIG. 2b, which will be deduced from the preceding equations. The path length through the cylindrical mass of food product, and hence its absorption, assuming it is homogeneous, will obviously vary across the jar in accordance with the circular function $2[r_b^2 - x^2]^{1/2}$, again assuming the x-rays are parallel. The absorption of different products may differ substantially. Curves $F_1$ and $F_2$ in FIG. 2b represent the absorption caused by two different goods. Curve $A_T$ in FIG. 2b represents the total absorption of the glass jar together with the food product of curve $F_1$.

During a typical horizontal scan line such as that shown at H in FIG. 2, which line is assumed to proceed from left to right, the video output signal lies at a low (black) level shown at $a$ in FIG. 2c when the camera is first unblanked. As the scanning beam reaches the background area portion of the stored image, the video signal rises to a maximum level, such as that shown at $b$. As the beam reaches an image portion representing the left side wall of the cylindrical jar, where a substantial thickness of glass results in substantial absorption, the video signal briefly decreases sharply, as indicated at $c$ in FIG. 2a. Then as the beam crosses image portions representing lesser thicknesses of glass and greater thicknesses of food product, the video signal will vary typically in the manner shown at $d$, assuming no foreign particle or substantial void is encountered. As the scanning beam traverses the increased thickness of the glass at the trailing edge, the video signal decreases as at $e$, then suddenly increases to the level shown at $f$ as background area is again encountered, and drops to level $g$ as background area is passed, until the camera is blanked at the end of the scan line. The mid-portion $d$ of the video level may be substantially flat as shown in FIG. 2c, or instead may be concave upward or concave downward, as indicated in FIG. 2d, depending upon the type of food product contained within the jar.

The camera video signal is applied to detection unit 20 throughout each inspection scanning field, and thus the detection unit will receive a plurality of successive video signals generally of the type shown in FIG. 2c as successive horizontal lines of the inspection scanning field are scanned. In the specific embodiment to be described the vertical sweep proceeds upwardly, so that the bottom of the jar is scanned first and the top or cap of the jar is scanned last during the inspection scanning field. In various other embodiments of the invention vertical scanning may proceed in the other direction, and indeed in some embodiments the scanning may proceed at a variety of different angles. The video signal shown in FIG. 2c differs from the video line signal provided by most television cameras in that it does not include a horizontal sync pulse, although that is not necessary to operation of the invention.

In FIG. 3a the camera video signal is shown applied via a buffer amplifier 30, which is assumed to be non-inverting, to a low-pass filter 31, which merely removes high frequency noise and thence to a first delay circuit 32 shown as comprising a 1.5 microsecond delay line. As will be explained below, the delay of circuit 32 is selected partly dependent upon the time required to scan across the thickened glass jar edge portion or side wall. Delay 32 may be made adjustable or similar delays of different time lengths may be switched in for different applications although the period of delay 32 must be related to various other timing periods, as will become clear below. The slightly-dalayed video signal from delay 32 is applied through clamping circuit 33 to log converter amplifier 34. Clamp circuit 33 is operated during the camera horizontal retrace for DC level control to provide a known-level input signal, the black level video signal then being provided by the camera, to log amplifier 34 at a predetermined time during the retrace interval. The camera output signal is substantially linearly related to received input light, and hence a given change in detected light varies the percentage change in the camera output signal in an amount dependent upon the absolute instantaneous video or light level. By provision of a logarithmic output versus input gain characteristic in log converter circuit 34, it may provide an output signal wherein a given amount of change represents a given percentage change in received light, irrespective of the absolute level of the camera tube output signal. Thus the provision of a logarithmic amplification characteristic automatically reduces detection sensitivity when the video level is high and the slope of the amplifier characteristic is low, thereby providing a defect detection sensitivity which is substantially constant as a scan line crosses a jar, even though the x-ray attenuation caused by the varying path length through the food product varies drastically across the jar, generally as a circular function, as mentioned above. It will be apparent that log amplifier 34 need not provide a mathemetically precise logarithmic charateristic, but only a reasonable approximation thereof. The output signal of log converter circuit 34 is applied to "gray circuit" 35, the function of which is to insert a pulse of known DC level into the video signal channel during the horizontal retrace period while DC restoration is accomplished. The use of DC-restoration and the insertion of the gray level signal, a signal roughly midway between the "black" and "white" video levels, are not crucial to the operation of the invention, but desirable in order to improve the operation of the system. Since clamping, DC restoration and logarithmic amplification are well-known video signal techniques, the details of clamp circuits 33 and 41, and logarithmic amplifier 34 are not shown. The output signal from delay circuit 32 is connected to the input terminal of log amplifier 34 through a conventional coupling capacitor (not shown), and clamp circuit 33 may comprise a simple transistor switch (not shown) which merely grounds the amplifier input terminal during the clamping interval, so that the coupling capacitor is then charged to the video black-level voltage. Gray circuit 35 may comprise an amplifier (not shown) connected to receive the log amplifier 34 output through a resistor (not shown), with a simple transistor switch operable during a gray drive operating period to apply a know voltage from a voltage-source (not shown) to force the amplifier 34 output to a known level.

The output signal from circuit 35 is applied through a first attenuator circuit 36 to a summing circuit 37, which receives as a further input signal a feedback signal from a second attenuator circuit 38. The sum output signal from circuit 37 is applied to a second delay circuit 39, shown as comprising a 63,492 microsecond delay line. It is assumed that 63,492 microseconds is the period of one horizontal deflection cycle, and hence delay circuit 39 is termed a "one-line" delay.

The output signal from delay 39 is applied via attenuator 38 to summing circuit 37. Since delay 39 provides a one line delay, it can be deduced that the input signal applied to delay 39 during a given horizontal scan line will comprise the instantaneous video signal from attenuator 36, plus the video signal from the next previous line attenuated by a factor of $\alpha$ by its passage once through attenuator 38, plus the video signal from the second previous line attenuated by factor $\alpha^2$ by its passage twice through attenuator 38, etc., where the attenuation factor of attenuator 38 is $\alpha$. If $e_i$ is deemed to represent the voltage level of the signal from attenuator 36 for a given point along a given scan line, and $e_{i-1}$, $e_{i-2}$, $e_{i-3}$ . . . etc. are deemed to represent the voltages which occurred during the next previous line, the second previous line, the third previous line, etc., at the same relative points along those previous scan lines, the output signal from summing circuit 37 may be written as: $e_i + \alpha\, e_{i-1} + \alpha^2 e_{i-2} + \alpha^3 e_{i-3} \ldots$ .

If attenuator 38 attenuates the delay 39 output signal by a factor of say 0.6, the signal applied to delay 39 will thus be $e_i + 0.6\, e_{i-1} + 0.36\, e_{i-2} + 0.216\, e_{i-3} + 0.1296 e_{i-4}$ . . . .

At the instant such an output voltage is applied to delay 39, its output voltage, which is delayed behind its input by one line, will be seen to include each term of the above expressions except the first, so that the delay 39 output voltage $e_c$ will equal $e_c = e_{i-1} + \alpha\, e_{i-2} + \alpha^2 e_{i-3} + \alpha^3 e_{i-4} \ldots$ or $e_c = e_{i-1} + 0.6\, e_{i-2} + 0.36\, e_{i-3} + 0.216\, e_{i-4}$ . . . assuming $\alpha$ is adjusted to equal 0.6. Thus during a given inspection scanning field, the output signal from one-line delay 39 comprises a composite video signal which is composed largely of the video from the line last scanned, somewhat less of the previous line which was scanned, and progressively less of further lines previously scanned. If attenuator 38 provides greater attenuation, i.e. its attenuation factor is less than 0.6, the signals fed into and out of delay line 39 will contain a larger percentage of "recent" video and lesser percentages of "older" video.

The output signal from delay 39 is applied as one input signal to differential amplifier 40, which receives the gray circuit 35 output signal as its other input signal. Amplifier 40 provides an output signal commensurate in magnitude and sign with the difference between its input signals. If the video signal $e_o$ from gray circuit 35 for a line presently being scanned corresponds to the composite video signal output $e_c$ from delay 39 representing previous scan lines, the voltage output from difference amplifier 40 will be zero.

Assume that the several scan lines which produce the voltages in the above expressions all passed through similar areas of the jar and the product, so that each of the voltages $e_i$, $e_{i-1}$, $e_{i-2}$, etc., were equal and had a value $e_e$. The positive feedback around delay 39 thus would cause an output voltage from delay line equal to $e_e + 0.6 e_e + 0.36 e_e + 0.216 e_e + 0.1296 e_e \ldots$ In order to properly compare the present line video level signal $e_o$ with the composite video signal $e_c$, attenuator 36 is provided to scale down the input to summer 37 by a factor of $(1-\alpha)$, or by a factor of 0.4 where attenuator 38 provides a scale factor of 0.6, thereby to compensate for the increased gain provided by the positive feedback around delay 39. It will be apparent that, if desired, one could eliminate (by-pass) attenuator 36 and instead amplify, (by a factor of $1/(1-\alpha)$ or 2.5 in the example chosen) the signal applied to comparator 40 from gray circuit 35 to achieve similar results. In the circuit shown, where attenuators 36 and 38 provide attenuation by fators of $(1-\alpha)$ and $\alpha$, respectively, the two attenuators are preferably gauged so that the value of $\alpha$ may be simultaneously adjusted for different applications. If attenuator 38 is adjusted to provide extreme attenuation, i.e. $\alpha$ is made extremely small, then attenuator 36 is adjusted to provide a gain of approximately unity, and in such a case each scan line will be compared with only the immediately preceeding scan line. The attenuators 36 and 38 may comprise simple switch-controlled resistor attenuators.

With attenuator 38 adjusted to provide appreciable feedback, the video signal level provided by delay 39 at a given instant during a given scan line thus will be seen to comprise a weighted average of the signals which occurred at coresponding instants during all of the previous scan lines of the inspection scanning field. Comparison of a given scan line with a weighted average of plural past scan lines, rather than comparison with merely the last previous scan line, allows gradual changes occurring in corresponding points along successive scan lines to be more readily detected. Assume a given point along four successive scan lines were to provide successive video values of 0.1, 0.2, 0.3 and 0.4 volts from circuit 35, and that a video value of 0.0 occurred at the corresponding points along all scan lines prior to the mentioned four. If no feedback is provided around delay 39 and attenuator 36 is passed, amplifier 40 will compare each line with only the last preceding line, and when it receives the 0.4 volt signal it will compare it with the 0.3 volt signal, and hence provide an output commensurate with their 0.1 volt difference. On the other hand, if feedback is provided, with 60 set at 0.6 for sake of an example, when gray circuit 35 provides the 0.4 volt signal, delay 39 will provide a composite signal equal to 0.4 (0.3 + 0.6 + 0.2 × 0.36 × 0.1) or approximately 0.1824 volts, and thus the difference between the signals received by amplifier 40 will be 0.4000–0.1824 or 0.2176 volt, exceeding the 0.10 volt difference which occurs without feedback, and thus providing increased ability to detect changes in corresponding points along successive scan lines.

The output signal of differential amplifier 40 is applied through clamp circuit 41 to positive comparator 42 and negative comparator 43. Clamp circuit 41 is operated during each horizontal retrace time to DC-restore the output signal from amplifier 40, so that a known DC level output from clamp 41 will represent a known difference in video level between the line next scanned and the weighted composite video signal representing lines previously scanned. Clamp circuit 41 maay comprise an amplifier (not shown) having its input terminal connected to receive the amplifier 40 output signal through a coupling capacitor (not shown) and its output terminal connected to comparator amplifiers 42 and 43, with a simple transistor switch (not shown) which is operative to ground the input terminal during the clamping interval, so that the coupling capacitor is charged to a known voltage. Each of comparators 42 and 43 comprises a circuit such as a high-gain fast-switching amplifier connected to receive a pair of analog input voltages and capable of switching between opposite polarity output voltage conditions to provide a boolean logic signal as the sign of the difference of its input voltages changes. Positive comparator 42 receives a threshold or reference voltage on line 44 from a control or threshold voltage generating means to be described and provides a logic 1 output signal to "positive reject" gate G1 through logic inverter I1 whenever the output voltage of difference amplifier 40 exceeds a level established by the reference threshold voltage applied to comparator 42, as would occur, typically, when a point along a given scan line has substantially less radiographic density than corresponding points along previous lines. Similarly, negative comparator 43 receives a threshold or reference voltage on line 45, and through logic inverter I2 provides a logic 0 output signal to detection gate G2 when the output voltage from amplifier 40 becomes less (more negative) than a level established by the reference threshold voltage applied to comparator 43, as would occur, typically, when a point along a given scan line has substantially greater radiographic density than corresponding points along previous lines. The magnitudes of the reference voltages applied to comparators 42 and 43 are varies as scanning proceeds through different vertically stacked zones of a jar, by means to be described.

If each elemental area in a given scan line is compared with the corresponding elemental area which occurred at the same horizontal position during the immediately preceding scan lines, it will be apparent that minute changes which occur from one line to the next may be easily detected. Furthermore, because no integration of the video signals is used for comparison, an abnormally transparent area cannot mask an abnormally dense area. Still further, assuming that the x-ray source intensity and camera tube gain do not change appreciably in the brief instant of one horizontal scan, it will be seen that detection is not appreciably affected by changes in source intensity or camera gain, since difference amplifier 40 does not respond to absolute values of the video signals, but rather the difference between video signals occurring during corresponding parts of successive scan lines.

As well as the video signal applied to buffer 30, the detection unit shown in FIGS. 3a and 3b receives several standard timing signals from the camera 16 including a horizontal sync pulse applied at terminal H, and a vertical sync pulse applied at terminal V. A blanking pulse is applied at terminal BL. The blanking pulse blanks camera 16 for approximately 16 milliseconds, i.e. for one cycle of a 60 hertz supply source, during approximately one-half of which cycle x-ray source 12 is energized. The horizontal sweep repetition rate of the camera is assumed to be 15,750 hertz, so that each horizontal cycle requires 63.492 milliseconds. The operation of the unit of FIGS. 3a–3b as horizontal scanning occurs may be best understood by reference to the waveforms show in the horizontal timing diagram of FIG. 4.

During the horizontal retrace interval the camera applies a negative horizontal sync pulse to terminal H, thereby providing a like positive pulse from interface amplifier A2 on line $\overline{H}$. Interface amplifier A2, vertical interface amplifier A12, and transistor T4 are provided merely to convert the camera output signals to appropriate TTL logic levels, and may be unnecessary in some applications. The circuits of FIGS. 3a and 3b also include a number of nand gates, indicated in conventional fashion as semicircles having a straight-line edge where input lines are connected, and an attached small circle indicating the output line. Each such gate provides a positive or logic 1 output voltage at all times except when each of its input lines receives a positive or logic 1 input voltage. As the pulse on line $\overline{H}$ swings negatively at the end of the camera horizontal sync pulse, it triggers monostable multivibrator, or "one-shot", or pulser P1, which is constructed to provide a pulse of approximately 2.0 microseconds, for example, which will be termed the "reset" pulse. Pulser P1, and numerous other pulses or monostable multivibrators to be mentioned (other than P6 and P7) each may comprise a conventional integrated circuit pulser, such as Texas Instrument Type 74121, for example. Pulsers P6 and P7 are similar, but preferably are a retriggerable type of one-shot, such as Type 74123. In FIGS. 3a and 3b a pulser input line which causes triggering upon receipt of a negative transition signal, such as the A1 or A2 input line of a Type 74121, is indicated by inclusion of a small circle, while a positive triggering input line, such as the B input of a Type 74121, omits such a circle. The upper output line of each pulser is the conventional Q output, which is positive or logic 1 during the pulser period, while the lower or $\overline{Q}$ output line represents the complement output. The period of each one-shot may be determined in accordance with standard practice by means of a respective external capacitor and adjustable resistance, neither of which are shown.

The fall of the mentioned horizontal timing signal on line $\overline{H}$ also triggers pulser P2, which has a period of 8 microseconds, for example. The output pulse from pulser P2 is applied to gray circuit 35, where it operates a transistor switch (not shown) to apply a predetermined voltage from a voltage-divider (not shown) to an amplifier (not shown) within gray circuit 35. The fall of the reset line after approximately 2.0 microseconds triggers clamp one-shot P5 for approximately 3 microseconds, providing a 3 microsecond positive pulse to clamp circuits 33 and 41. The clamping control pulse from pulser P5 is thus made to occur in between the ends of the gray level insertion control pulse from pulser P2, so that clamping and DC-restoration occurs while a gray level voltage is applied to the video channel.

As reset pulser P1 is triggered, the drop of its complement output line clears JK flip-flop 48, and the rise of its reset output line triggers "left limit" pulser P3, providing a logic 0 output pulse on line $\overline{N}$ for typically 15 microseconds, and as pulser P3 resets the rise of its complement output triggers "right limit" pulser P4, providing a logic 1 on its M output line for approximately 30 microseconds. The period of left limit pulser P3 is adjusted by the operator so as to establish a vertical slice or area at the left side of the scanning field in which defects or an adjacent jar will not be detected, and the period of right limit pulser P4 is adjusted to establish a middle section of the the field within which defects in a jar to be inspected will be indicated, and rightwardly from which neither defects not adjacent jars will be indicated. As will be seen below, defects will be indicated only when pulser P4 is set and line M is up, or logic 1. Since pulser P4 is not set until pulser P3 resets, line M will be low and defects will not be indicated while pulser P3 is set, and again, defects will not be indicated after pulser P4 resets. In FIG. 2, assuming the outer solid-line rectangle indicates the bounds of the scanning raster, oneshots P3 and P4 typically might be adjusted so that one-shot P4 is set during the interval between lines $M_i$ and $M_t$. Providing limits of detection in such a manner allows the system to ignore jars adjacent to the jar being inspected even though the adjacent jars extend partly into the scanning field, as will become clear below. It is necessary, of course, that the period of pulser P4 be long enough to equal or exceed the interior width of a jar if the entire contents of the jar are to be inspected.

The fall of the reset line also triggers pulser P8, the period of which is also adjustable, and as pulser P8 resets it triggers pulser P9, the period of which is also adjustable. The period of pulser P8 is adjusted, in relation to horizontal sweep, so that pulser P8 will reset as the camera beam reaches a horizontal position corresponding to the left edge of a camera target imperfection, and the period of pulser P9 is adjusted, also in relation to horizontal sweep speed and the horizontal width of the target imperfection, so that pulser P9 is set while, and only while the camera beam scans between horizontal positions corresponding to the left and right edges of the target imperfection. In FIG. 2 a target imperfection (of greatly exaggerated size) is shown at T1, and lines shown at HT indicate the period during which one-shot P9 is set. The output HT from pulser P9 is applied to nand gate G3, which receives a similar signal on line VT specifying the vertical position and vertical height of the target imperfection, as indicated by lines at VT in FIG. 2, and thus gate G3 is enabled to provide an output to prevent or inhibit defect indication while the camera target imperfection is being scanned. It will be apparent that pulsers P8 and P9 (and similar pulsers, P14, P15 in the vertical system) may be duplicated to prevent defect indication while additional target imperfections are scanned.

The camera video signal from buffer 30 is applied to an edge-detecting circuit 46 shown as comprising capacitor C1, resistor R1, diode X1 and amplifier A1. Amplifier A1 is provided with positive feedback so that its output line (labelled $\overline{E}$) will swing from one logic level to the other whenever its input voltage crosses a threshold established by adjustment of potentiometer VR1. Operation of amplifier A1 is best understood by reference to the waveforms of FIG. 6, wherein the upper waveform illustrates the camera or buffer 30 video output signal during a typical scan line, the waveform 46 represents the voltage on the inverting input line of amplifier A1, and the $\overline{E}$ waveform represents the logic output on line $\overline{E}$.

As the scanning beam reaches the edge of the bright background area and the input video level rises sharply as at $a$ in FIG. 6, the amplifier A1 output line $\overline{E}$ drops quickly to its logic 0 level. The conduction of diode X1 limits the A1 input voltage to the forward drop (e.g. 0.4 volt) of diode X1, and capacitor C1 charges substantially to the maximum level (shown at $b$) which the video signal reaches as background area is scanned. Then as the scanning beam intercepts the edge of the jar portion of the image, the sharp drop in the video signal causes amplifier A1 to switch to its opposite state. The threshold of amplifier A1 is adjusted so that amplifier A1 will change state at a level which is below the maximum background video level, but above the video level which occurs while portions of the jar are being scanned. Thus the voltage on line $\overline{E}$ goes low as background at the left of the jar is scanned, rises rapidly as soon as the left edge of the jar is intercepted, remains high at a logic 1 value as the scan line proceeds across the jar, and drops sharply as the beam leaves the right edge of the jar and encounters background area on the right side of the jar.

As the scan line first intercepts background area to the left of the left edge of the jar, the fall of line $\overline{E}$ disables nand gate G4 and sets one-shot P7 providing a pulse on line R. That particular pulse on line R serves no present function and its presence may be ignored for the moment. It may be noted, however, that line X is driven low each time background area is intercepted, with a delay determined by the period of R one-shot P7, which will become important as the opposite edge of the jar is scanned. When the $\overline{E}$ line falls as background is intercepted, gates G5 and G6 would both be disabled so that gate G7 would lower line X, but the raising of line R while P7 is set enables gate G6, so that line X does not fall after background is intercepted until P7 resets. As P7 resets, scanning continues with line X lowered.

The scan line then continues to progress across the background area at the left side of the jar, and the next event of importance is that it enters the central area, determined by adjustment of the M one-shot P4, wherein detection is intended to occur, the central area being bounded by lines $M_t$ and $M_t$ in FIG. 2. As M one-shot P4 is set, with line X lowered, it will be seen that gate G8 will be enabled, thereby setting JK flip-flop 48 to raise its Y output line. As will be seen below, line Y must be raised for any detected defects to be registered.

Now assume that an extraneous jar JL to the left of the jar J intended to be inspected protrudes into the M central area, as shown in FIG. 7. At the time M one-shot P4 is first set, with a portion of jar JL being scanned, the $\overline{E}$ line will be high, as explained in connection with FIG. 6. With line $\overline{E}$ high, gate G5 will be enabled, thereby preventing gate G7 from lowering line X. With line X high, gate G8 will not be enabled when the central inspection area is reached and M one-shot P4 is set, and hence JK flip-flop 48 will not be set, line Y will not be raised, and no defect detection can be registered as the scan line passes through jar JL. Thus the circuit described will be seen to require that line X be low, i.e. that background be scanned, during an initial portion of the central inspection area while M pulser P4 is set, before any defect registration can occur, and hence any defects which are detected in portions of jar JL are ignored. However, even though any defects occurring in partially scanned jar JL are ignored, the partial presence of jar JL does not prevent complete detection of defects in central jar J in FIG. 7, which is an important feature of the invention. As a scan line passes the right edge of the jar JL and encounters background, the lowering of line X then will cause JK flip-flop 48 to be set, so that a defect detected as the line passes through central jar J will be registered.

Now assume that the scan line progresses through background area toward jar J. Irrespective of whether the scan line had previously passed through jar JL, JK flip-flop 48 will be set. As the scan line intercepts the left edge of jar J, line $\overline{E}$ will rise, as explained in connection with FIG. 6, and will remain high as the scan line passes across jar J. The rise of line $\overline{E}$ will be seen to set "left edge" one-shot P6. If one-shot P6 were not set, the rise of line $\overline{E}$ would result in gate G5 being enabled and gate G6 being disabled, so that gate G7 would raise line X. However, the setting of one-shot P6 results in G5 and G6 both being disabled, so that line X continues to remain low during the period of one-shot P6. Thus line X, as well as being driven low when background is intercepted with a delay equal to the period of P one-shot P7, is also maintained low after the scan line passes from background to jar, for a period equal to that of L one-shot P6. Now if the period of one-shot P6 is adjusted to equal the time $t_g$ required to scan through the thickened glass portion or side wall of the jar, plus the delay (e.g. 1.5 microsecond) of delay 32, plus any appreciable delays between delay 32 and the output of gray circuit 35, it can be seen that line X will rise to enable registration of a defect, at precisely the time video representing product just inside the left wall of the jar is reaching differential amplifier 40, and that any operation of comparators 42 and 43 prior to that instant, such as when the scan line was crossing the thickened-glass left side wall of the jar, will not cause registration of a defect.

With line X now high and JK flip-flop 48 set, as the scan line passes through the central jar, gate G9 will be enabled, disabling gate G10, and resulting through gate G11 and inverter I6, in a logic 1 signal being present on line HD to conditionally enable main detection gate G12. Then, assuming logic 1 signals are applied to gate G12 from inverter I10 and "target imperfection" gate G3, any defect which causes a logic 1 defect-signal through gate G2 from comparator 42 or comparator 43 will enable main detection gate G12, thereby setting flip-flop 52, to "temporarily" register the defect.

As the horizontal scan line passes through the thickened glass right side wall of the jar and again encounters bright background, line $\overline{E}$ will again swing low, as explained in connection with FIG. 6. As happened before, the negative transition of line $\overline{E}$ will set one-shot P7 and temporarily raise line R, and, as previously explained, will delay the lowering of line X for the period of one-shot P7. Now, if the period of one-shot P7 is adjusted to be less than the period of delay 32 (plus any appreciable delay between delay 32 and gray circuit 35), it may be deduced that line X will be lowered to inhibit registration of defects shortly before video representing product at the inside edge of the thickened glass right side wall of the jar is reaching differential amplifier 40, and that later video representing the right wall itself will not cause registration of a defect.

As line X swings low, gate G9 is enabled, thereby enabling gate G10 to lower the "release" line, which is connected to the clock input of D flip-flop 51. If one or more defects have been previously temporarily registered during the scan line, so that flip-flop 52 was previously set and line A raised, the lowering of the release line sets flip flop 51, thereby raising line B. As will be seen below, line B then will remain high until the end of the inspection field, and its logic 1 condition used to provide a reject output signal, to eventually operate a conveyor gate or the like. After the release line is driven low, as the scan line continues across the background area on the right side of the jar, the M one-shot P4 which defines the central inspection area will reset, disabling gate G10 and raising the release line, and then the scan line will continue to its end, and retrace will occur in conventional fashion.

Now, assume instead, as shown in FIG. 7, that a second extraneous jar JR protrudes into the right side of the desired inspection area M. While flip-flop 48 prevented defects in a left-side adjacent jar from being registered by reason of flip-flop 48 not being set, that flip-flop cannot provide a similar function for a right-side extraneous jar since it will have been set just before the central jar J was intercepted by the scan line. Thus as the scan line crosses the right-side extraneous jar, line HD remains high and a defect noted in the right-side jar will cause flip-flop 52 to be set. However, the X line will remain high as the right-side jar is partially scanned, until after M one-shot P4 resets at the right side of the central inspection area. With the X line high prior to the reset of one-shot P4, gate G9 is enabled to disable gate G10, thereby holding the release line up, and after one-shot P4 resets gate G10 remains disabled, continuing to hold the release line up, and hence even though a defect in the right-side adjacent jar can set flip-flop 52, that defect indication will not be released or transferred to flip-flop 51, and hence it cannot cause a final output reject indication. At the end of each horizontal detection interval, the fall of line HD clears flip-flop 52 in preparation for the next scan line.

The vertical control system largely shown in FIG. 3b may be best understood by simultaneous reference to the waveforms of FIG. 5. The camera is assumed to scan with a standard vertical sweep repetition rate of 60 hertz, and a negative-going pulse is applied at that frequency to terminal V, so that inverting interface amplifier A12 provides a positive pulse every 1/60th second on line $\overline{V}$. The fall of each pulse on line $\overline{V}$ triggers one-shot P11, which may have a period of 700 microseconds, for example. Prior to the arrival of a jar in the inspection zone, the repeated triggering of one-shot P11 has no effect other than to insure that JK flip-flops 57 and 58 are cleared if they had been set during the inspection of a previous jar. Upon the arrival of a new jar in the inspection zone, a positive blanking pulse is applied to terminal BL for approximately 1/60th of a second, or one full cycle of the 60 hertz line source, and the X-ray source is turned on during one-half or the other of that cycle. The positive blanking pulse turns on transistor T4 during that cycle, lowering the T4 collector, so that the reset of one-shot P11 during that cycle sets flip-flop 57. No further switching occurs in the vertical system then until the end of that cycle, except that the blanking pulse terminates. Then, as well as again triggering one-shot P11, the next pulse on line $\overline{V}$ at the beginning of the next 1/60th second cycle enables gate G15, briefly lowering line VCL to initiate detection during the inspection scanning field. Since the blanking pulse has been terminated, the reset of P11 will clear flip-flop 57. The rise of line $\overline{V}$ at the beginning of that 1/60th second cycle enables gate G15, briefly lowering line VCL to generally initiate detection during the inspection scanning field, as previously mentioned, and the fall of line $\overline{V}$ again triggers one-shot P11. Next, as P11 resets, flip-flop 58 is set, because flip-flop 57 was in a set condition just prior to the time of P11 reset, and flip-flop 57 is cleared, because the blanking pulse was terminated prior to that time. Flip-flop 58 then remains set during the inspection scanning field. If, during the inspection scanning field a defect is registered, so as to raise line B as previously explained in connection with horizontal scanning, then at the end of the inspection scanning field the pulse on line $\overline{V}$ will be seen to enable gate G18, providing a positive reject pulse on the "reject" line from inverter I9.

The brief lowering of line VCL at the beginning of the inspection scanning field sets one-shots P12 and P14. Cascaded one-shots P12 and P13 function to control the vertical detection interval in generally the same manner that cascaded one-shots P3 and P4 determine the horizontal bounds of defect detection. Thus one-shot P12 is adjusted to reset at a vertical location below which detection is not desired to occur. The reset of P12 sets P13, the period of which is adjusted to define a vertically central area within which detection may occur, such an area being indicated by lines VD1 and VD2 in FIG. 2. Thus one-shot P13 conditionally enables main detection gate G12 via gate G14 and inverter I10 as a desired vertically central area is scanned, and the subsequent reset of one-shot P13 disables the main detection gate G12 as a desired upper limit (shown at line VD2 in FIG. 2) of the detection area is reached. Cascaded one-shots P14 and P15 are adjusted to define in a vertical sense, the edges of a target imperfection, in the same manner that one-shots P8 and P9 define the horizontal edges of the target imperfection, and thus, while one-shot P15 is set, and one-shot P9 is set, gate G3 is enabled to disable main detection gate G12 during the interval indicated by lines at VT in FIG. 2.

As P12 resets at the lower limit (shown at VD1 in FIG. 2) of the area in which defect detection is to be registered, as well as setting the "vertical height" one-shot P13, it also sets one-shot P16, the first of three cascaded "zone-generator" one-shots P16–P18, which are set in sequence as vertical scanning proceeds upwardly, P17 being set as P16 resets, and P18 being set as P17 resets. Thus each of one-shots P16 to P18 set during a different one of three vertically-stacked detection zones. When P18 resets at the end of the third zone, gate G16 will be enabled for the remaining time that one-shot P13 is set, so that presence of a logic 0 signal from gate G16 defines an uppermost fourth zone. In FIG. 2 four typical zones are indicated by dimensions Z1 to Z4. It should be apparent that more or fewer than four zones may be provided, if desired, by mere duplication or deletion of parts of the nature shown.

As one-shot P16 is set during zone 1, its lowered complement output line turns on transistor switch TS1 to ground the upper end of variable resistance R2, and when one-shot P17 or P18 is set or gate G16 is enabled during the other zones, in each case one or two similar switches operate to similarly ground respective variable resistances. Transistor T1 applies a temperature-compensated voltage to the bases of transistors T2 and T3. Transistor T2 thereby applies a positive current to line 57, and transistor T3 applies a positive current to line 58. When none of switches TS1 to TS4 is closed, the current from transistor T2 provides a large input voltage to amplifier A9 via an input resistance 55, which includes some low-pass filtering, thereby providing a large negative output voltage from inverting amplifier A9. When any one of transistor switches TS1 to TS4 is enabled or closed during a respective one of the four vertical zones, the connection of line 57 through the resistance associated with the closed transistor switch diverts some of the current from line 57, thereby decreasing the magnitude of the negative voltage output provided by amplifier A9. Thus amplifier A9 may apply a different magnitude of negative reference voltage to comparator 43 during each of the four zones, with the different magnitudes being readily adjustable, and adjustable independently of each other, by mere adjustment of the four variable resistances associated with switches TS1 to TS4. It is important to note that provision of an upper zone having a given sensitivity just below the level to which each jar should be filled with product will allow the system to reject bottles which are insufficiently filled.

Input current to non-inverting amplifier A10 is controlled in a similar manner to provide a positive reference voltage from amplifier A10, although only two switches and resistors are shown connected to line 58, so that current is diverted from line 58 only during zones 2 and 3, and the positive reference voltage from amplifier A10 lies at a high value during zones 1 and 4 of the inspection field, as well as before and after the inspection field. In the specific embodiment shown, the magnitude of the positive reference voltage during zones 1 and 4 is irrelevant, since detection of positive defects (e.g. voids) is intentionally in those zones, with gate G17 being disabled, so that gate G1 can disable gate G2 to enable main detection gate G12 only during zones 2 and 3. Thus during zones 2 and 3, whenever the output signal from difference amplifier 40 applied to comparator 42 through clamp circuit 41 exceeds (i.e. is more positive than) the positive reference voltage applied to comparator 42 by amplifier A10, which would occur when an abnormally transparent image portion is scanned, the positive comparator 42 output line swings negative, and the inverter I1 positive output enables gate G1, thereby applying logic 1 from gate G2 to enable main detection gate G12. Indication of "positive defects", i.e. voids or abnormally transparent areas, is prevented during the uppermost zone 4 so that the entire contents of a jar may be inspected up to the very top of the product, without causing erroneous rejection. In FIG. 2, if the top of the food product is not level, it will be seen that a plurality of "voids" will be detected as a scan line intersects various portions of wavy line P', and even if the top of the product is level, positive comparator 42 will provide an output signal as amplifier 40 compares the video from the first bright line above the top of the product with the darker video which was previously obtained from prior scans through the product and which is then circulating in one-line delay 39. Preventing indication of only positive rejections during uppermost zone 4 still allows negative defects, such as glass or metal particles to be detected up to the very top of the product, however. Since indication of positive defects is prevented in lowermost zone 1, the change in video between the last scan line through the bottom of a normal jar and the next high scan line through the food product just above the bottom of the normal jar will not cause an erroneous reject indication. Furthermore, such an arrangement allows negative defects to be detected at the very lowest positions occupied by food product,. while avoiding false reject indications which otherwise might occur due to either a central hump prevalent in the bottoms of many jars, or slightly increased glass thickness wall thickness near the bottom of many jars. During any one of zones 1 to 4, whenever the output signal from amplifier 40 is more negative than the negative reference signal applied to negative comparator 43, which would occur when an abnormally dense image portion is scanned, comparator 43 provides a positive or logic 1 output signal and inverter I2 or logic 0 signal, disabling gate G2 to enable main detection gate G12.

It will be apparent that main detection gate G12 can be enabled to temporarily register a defect in flip-flop 52 only if gate G14 is enabled, which requires that JK flip-flop 54 be cleared. That flip-flop will be cleared by the fall of the horizontal sync pulse on line H at the beginning of each horizontal scan line if JK flip-flop 53 is cleared. Flip-flop 53 will have been cleared by the reset pulse which occurred at the beginning of the preceding scan line, and will have remained cleared so long as inverter I7 did not apply a negative signal to the clock input line of flip-flop 53 during that preceding line. The video signal is shown applied from gray circuit 35 through low-pass filter 52 to "bottom detector" amplifier A2, which is provided with positive feedback and a positive bias on its non-inverting input line, so that is provides a negative or logic 0 output voltage whenever it receives an input signal from circuit 35 representing a given brightness or above, but provides a logic 1 signal if the video signal level falls below a selected value. Thus as a line is scanned near the bottom of the jar, if the scan line crosses a dark image area representing conveyor structure, the thick glass bottom of the jar, or a hump in bottom of the jar, the decrease in the video signal level causes an increase in output voltage of amplifier A2, thereby providing a negative-going logic signal from inverter I7 to set JK flip-flop 53. Then at the end of that scan line, the fall of the next horizontal sync pulse on line H causes JK flip-flop 54 to be set, disabling gates G14 and G12, so that no reject pulses can pass through main detection gate G12 during the next scan line. Thus it will be seen that as successive lines are scanned, starting at the bottom of the jar and progressing upwardly, no defect can be registered for any scan line, until the line following the first line in which no very dark area has been intercepted. Such an arrangement will be seen to be operative to prevent defect indication as scanning of an article is initiated, thereby making a system which compares successive scan lines practical. The video level at which amplifier A2 switches is made adjustable for different applications by adjustment of the bias voltage applied to that amplifier.

The reject output of line of inverter I9 is shown connected to the input line of a shift register SR, which receives periodic shift pulses at a rate synchronized with conveyor speed, and thus a reject pulse registered in the shift register travels along the shift register at a speed commensurate with that of a rejected jar. Shift register SR is provided with a number of stages in relation to the rate of the shift pulses, so that a reject pulse relating to a given jar reaches the shift register output line to set pulser P20 at the same time that a defective jar reaches the conveyor rejection gate 22 (FIG. 1), so pulser P20 provides a pulse via amplifier A11 to operate reject solenoid 21 to remove the defective jar from the conveyor. The reject line pulses also may be connected to a counter C0, so that a count of defective articles may be maintained, and may operate various forms of visual or audible alarms or indicators.

While a reject pulse is not passed through output gate G18 until the end of the inspection scanning field, line B, which is raised as soon as a defect is detected, is connected to trigger one-shot P19, the output signal of which is connected through the video mixer to temporarily brighten the monitor when a defect is detected, and thus an operator or attendant may verify, by viewing one or more bright lines on the monitor with a defective jar placed in the inspection zone, that defects will be properly detected. The output lines from the zones 1 and 3 pulsers P16 and P18 are also routed to the video mixer to vary the brightness of the monitor display while those zones are scanned, and thus the operator may readily observe which portions of a jar each zone covers, and adjust pulsers P12, P13 and P16 to P18 so that each zone covers a desired vertical band of the jars which are to be inspected, with alternate brightened bands being superimposed on the jar image visible on the monitor. For set-up and adjustment purposes, a simple timer (not shown) is provided to supply periodic pulses when the conveyor is not running, to simulate pulses from presence sensor 14. An image of a jar then located in the inspection zone will appear on the monitor.

The vertical timing system illustrated in FIGS. 3a and 3b assumes that the camera vertical sweep system is cynchronized with the 60 hertz line source, so that the vertical sync pulses on line V occur quite near alternate zero crossings of the line source. In FIG. 8 the alternating source is connected through diode X8 and resistor R18 to a conventional Schmitt trigger 80 to provide a square wave on line ST in phase with the line voltage. The timing of the circuit of FIG. 8 is illustrated by waveforms in FIG. 8a. Line PS carries a signal from the presence sensor 14 (FIG. 1) which goes to logic 1 for a brief period each time the presence of a jar is sensed, thereby setting one-shot P21 to apply a 10 millisecond pulse to the D input line of flip-flop 81, which may comprise a Type 7474 D flip-flop. The 60 hertz square wave on line ST is applied to the clock input of flip-flop 81, which is positive-edge-triggered. Thus flip-flop 81 is set by the first positive transition on line ST after a jar is sensed. At the next positive transition of line ST, one-sixtieth second later, flip-flop 81 will clear, since the period (10ms) of one-shot P21 is less than one-sixtieth second. The Q output on line BL may be used to blank the camera scanning beam. The negative transition of the $\overline{Q}$ or complement output of the flip-flop triggers one-shot P22, which also has a period of 10 milliseconds. The 10 ms. pulse from P22 drives a commercially-available solid-state relay 82 comprised of an optical isolator and a triac, thereby applying line voltage to a transformer (not shown) of the X-ray source 12. Use of a 10 ms. pulse insures that the triac is turned on for two half-cycles. X radiation is emitted by the source during one half-cycle, while the transformer of the source is reset during the other half-cycle.

In FIG. 8b a thyristor is rather similarly controlled by one-shot P23 to connect a DC voltage stored in capacitor C8 to the x-ray source, the input circuit of which includes a transformer, only the primary winding of which is shown at PW. One-shot P23 may be triggered by the signal from the presence sensor. In between the times at which one-shot P23 is triggered, capacitor C8 is charged through resistance R8 from a DC supply which may be completely conventional. When the thyristor is turned on by a brief pulse from one-shot P23, capacitor C8 and the transformer primary winding comprise a closed LC circuit loop which oscillates or "rings", and after a large initial surge of current into the primary winding, the current flow and the voltage in the loop reverse, turning off the thyristor. The duration of the x-ray pulse is determined by the time-constant of the LC circuit shown.

Video mixer 23 receives a group of logic signals which modulate the video signal from delay 32 to provide indicia in the image provided on a conventional television monitor by selectively brightening certain scan lines or portions thereof. The monitor is synchronized by sync signals derived by the camera in conventional fashion. As shown in FIG. 9, the mixer may comprise a simple summing amplifier A23 which receives the video signal from delay 32 and terminal 23a on its input line, together with currents applied through input resistors R21–R24 from logic gates and a transistor T-20 controlled by the reject bar one-shot P19 of FIG. 3a. Assuming marker switch SM is closed, it will be seen that while either zone 1 or zone 3 of the four vertically stacked zones is being scanned, gate G25 will provide a logic 1 output, and the gate G26 output hence will go low during that portion of a scan line when line HD is high, decreasing the positive input current otherwise applied to summing amplifier A23 through resistor R23 from voltage divider R25, and thereby raising the average level of the amplifier A23 output to brighten the monitor trace. In similar fashion, a lowered output from gate G27 will further brighten the monitor by decreasing the current applied through resistance R22 when lines HD and VD are both logic 1, so that the area in which detected defects will be registered will be readily visible on the screen, and a lowered output from gate G28 will further brighten the monitor screen to indicate the location of the target imperfection where defect registration is not provided. Opening of marker switch SM will, of course, remove such indicia from the monitor screen. When a detected defect causes one-shot P19 to be temporarily set, the input signal from P19 to the base of transistor T20 cuts off that transistor, lowering its collector voltage and causing the monitor trace to be brightened until P19 resets. The period of P19 is ordinarily made as long as one or two scan lines, and hence a bright line will appear on the monitor at the level of the detected defect, or more precisely one or two scan lines above the level of the defect. Closure of switch RBS will, of course, remove such brightened lines from the monitor display. With indicia of the type described provided in the monitor display, one may readily adjust the periods of one-shots P3, P4, P6, P7, P8 and P9 to insure that the defect registration will occur in desired areas of an article to be inspected, and only in those desired areas.

While the precise system disclosed in FIGS. 3a and 3b is arranged to ignore any partial jar portions which may extend into the detection zone from either side and to indicate defects solely in a single central jar, it should be noted that by extension of the disclosed principles, and a doubling-up of some of the logic circuits, the invention may be modified so that though it will ignore any partial jar portions, it will detect defects in two or more jars situated entirely within the scanning field. Also, the camera may be arranged to scan only a fraction of the width of its target during a first inspection scanning field, and then with mere imposition of a horizontal positioning bias signal made to scan another fraction of the width of the target, so that image portions containing different articles are scanned each time.

While an important advantage of the invention is that it need not integrate video signal levels to detect foreign particles or other defects, one should note that video signal integration may be used in conjunction with the invention, for checking purposes, and to obtain added information concerning the product.

Should the x-ray source or camera video fail, the system of FIGS. 3a and 3b as thus far described will scan a uniformly dark image and fail to detect jars which should be rejected. The complement output signal from JK flip-flop 54 may be applied to a nand gate (not shown) together with an inverted version of the gate G16 output, for example, to provide a negative-going logic signal if flip-flop 54 has not been set by the time the uppermost zone is reached, and that signal may be used to provide any desired form of visual or audible alarm, or used to halt the conveyor drive motor.

While the reference voltages applied to comparators 42 and 43 have been shown as having constant values throughout a given zone of the group of vertically-stacked zones, it is within the scope of the invention to provide reference voltages which vary across portions of, or all of the scanning field, in either a vertical sense or a horizontal sense, or both. If the camera vertical sweep waveform is a positively-increasing ramp with a negative retrace and is connected to terminals 61 and 62 in FIG. 3b, it will be apparent that in addition to the variation in the reference voltages provided by switches TS1 to TS6, the reference voltages will tend to gradually increase in magnitude as the scan field proceeds upwardly, and use instead of a negatively-increasing ramp would of course cause the reference voltages to generally decrease as a field proceeds upwardly. It will now be apparent that four one-shots (not shown) connected to enable a gate in generally the same manner as the four one-shots shown used to blank out the target imperfection may be used to operate one or more switches connected like switches TS1 to TS6 to allow either the positive or the negative reference voltage, or both of them, to be automatically decreased or increased in any rectangular sub-portion of the rectangular detection area defined by the set times of one-shots P4 and P13.

In FIG. 10 a counter CO1 is reset by the V signal at the beginning of each vertical field, and as a scanning field occurs the horizontal sync pulses advance the counter. Selected groups of counter output lines may energize various gates, only two of which are shown, to close switches such as TS1 and TS2 in FIG. 10, which may be connected to resistors as generally shown in FIG. 3b, to provide different reference voltages in a variety of different zones.

It will be apparent at this point that portions of the camera horizontal sweep waveform also may be applied to the reference voltage generating circuits to provide reference voltages which vary horizontally across the scanning field in a variety of different ways.

FIG. 12 illustrates a modification which may be made to FIG. 3b to overcome erroneous rejections which otherwise may sometimes occur due to the limited speed or bandwith of the video circuits, which may prevent the video signal from falling as rapidly as it should as the scanning beam enters the left edge of the product. In FIG. 12 switch TS12 is closed when line HD is low as the scan line approaches the left edge of the product, so that capacitor C12 is discharged. When line HD rises as the left edge of the product is encountered, the opening of switch TS12 allows capacitor C12 to charge. During the brief interval while C12 charges, the currents to lines 57 and 58 will initially be higher, thereby causing the reference voltages provided by amplifiers A9 and A10 (FIG. 3b) to be initially greater and then to fall to a normal value when C12 is largely charged. Capacitor C12 and resistor R23 are typically selected so that the reference voltages will fall from their initially higher value with a very small time-constant, of the order of 0.5 microsecond. Thus the detection sensitivity will be temporarily reduced for a brief period as the scan line enters the left edge of the product inside the jar.

In certain applications, such as those wherein large ridges or changes in glass thickness occur along the vertical length of the jar which is to be inspected, it becomes desirable to vary the delays provided in certain portions of the system of FIGS. 3a and 3b as thickened glass portions of the image are scanned and FIG. 11 illustrates one manner in which certain portions of FIG. 3a may be modified for such a purpose. In FIG. 11 a signal labelled Z is assumed to be logic 1 whenever a zone of the jar having an increased thickness is being scanned. It will be apparent that the Z signal may be derived in the same manner as any of the four zone signals shown derived in FIG. 3a, or, if desired, by use of a gate (not shown) driven by selected output lines of counter CO in FIG. 10. During normal scanning, when line Z is logic 0, transistor switch TS11a is closed, thereby shorting resistance R11a, so that the period of L one-shot P6 is determined by the RC time-constant provided by resistance R11 b and capacitor C11a, and simultaneously, transistor switch TS11b is open, so that the period of R one-shot P7 is determined by the time-constant of resistance R11c and capacitor C11b. However, when line Z is raised, switch TS11a opens, thereby increasing the P6 period, and switch TS11b closes, thereby reducing the P7 period, thus increasing the width of the side wall portions which are not allowed to be detected as defects. It will be apparent that a pluality of switches may be used at each of pulsers P7 and P6, with different such switches controlled by respective Z or zone signals to provide several different side wall widths. Also, it will be apparent that the periods of the P6 and P7 one-shots may be varied by switching capacitors rather than resistors.

In the system described in connection with FIGS. 3a and 3b, B flip-flop 51 is set if a foreign particle is detected in a single scan line. In some applications it becomes desirable to reject a jar only if particles are detected in plural scan lines. In a modified arrangement partially illustrated in FIG. 13 flip-flop 52 functions just as in FIG. 3a. If a defect is detected in a given scan line so that flip-flop 52 is set to raise line A, the lowering of the release line at the end of the horizontal detection interval then enables gate G43 and applies an input pulse to binary pulse counter SD. Selected output lines from the counter are connected to gate G42, and hence that gate is enabled to set flip-flop 51a only if a selected number (or more) of defects are detected in a given field. The set output of flip-flop 51a is connected to gate G18 of FIG. 3b in lieu of the flip-flop 51 output, and the vertical clock pulse resets counter SD and flip-flop 51a at the end of the field. Thus with the modification of FIG. 13 a jar will be rejected only if some selected number of defects is exceeded, irrespective of where such defects occur in the detection area. In an alternative modification illustrated in FIG. 14, the output of main detection gate G12 is instead applied via an inverter to flip-flop 52c, so that a defect which occurs in a given line will set flip-flop 52c when the release pulse occurs near the end of that line, raising line B to apply an input signal to shift register SR2, which is shifted between each scan line by the reset signal previously described. Output signals from a plurality of selected stages of the shift register are connected to gate G46. If the output lines of successive stages are connected to gate G46, as ordinarily will be the case, then gate G46 will be enabled to apply a reject pulse to gate G18 only if defects are detected in a selected number of successive scan lines.

While the system shown in FIGS. 3a and 3b compares each difference voltage from difference amplifier 40 with a single threshold value, it is within the scope of the invention to compare each with two or even more threshold values. In FIG. 15 the output voltage of amplifier 40 is shown applied to two banks of comparator amplifiers, one bank (42a–42c) of which receives positive reference voltages and the other (43a–43c) of which receives negative reference voltages. The reference voltages applied to terminals +R and −R may be derived in any of the ways suggested above. A positive output pulse from amplifier 40 will raise line $a$, or lines $a$ and $b$, or lines $a$, $b$ and $c$, depending upon whether it exceeds in magnitude the voltage at terminal $a'$, and at $b'$, or that at $c'$, respectively, of the positive reference voltage divider, and a negative pulse from amplifier 40 will raise line $d$, or lines $d$ and $e$, or lines $d$, $e$ and $f$, depending upon whether it exceeds in magnitude the voltage at terminal $d'$, that at $e'$, or that at $f'$, respectively, of the negative reference voltage divider. Thus a logic 1 will occur on line $a$ upon detection of an elemental area representing a modest increase in radiographic density, while a greater decrease will raise both lines $a$ and $b$, and a further greater decrease will raise all three of lines $a$, $b$ and $c$, and signals will occur in similar manner on lines $d$, $e$ and $f$ upon detection of various levels of increases in radiographic density. Lines $a$ and $d$ are connected to an OR gate G15a, so that and gate G12a will be enabled if a modest increase or decrease in density occurs along a given scan line, and then occurrence of the release signal near the end of the line will cause flip-flop 52a to be set and a logic 1 to be registered in shift register SRA. Signals are stored in shift register SRB in a similar manner for defects which fall within an intermediate range of change in density, and such defects also, of course, cause signals to be stored in register SRA. Large increases or decreases in density which cause comparator 42a or 43a to switch will cause signals to be stored in all three shift registers in FIG. 15. Output lines from various stages of each shift register are connected to respective gates G17a to G17c, so that gate G17c will be enabled if large changes in density occur during relatively few successive scan lines, gate G17b will be enabled if intermediate-magnitude changes in density occur during a somewhat larger number of successive scan lines, and gate G17a will be enabled if comparatively small changes in density occur during a still larger number of successive scan lines.

While the system disclosed in detail in FIGS. 3a and 3b makes no final indication of whether a given defect represents an abnormally dense area or an abnormally transparent area, it should be apparent that the positive and negative comparators 42 and 43 may be arranged to enable separate main detection gates (similar to G12) followed by separate pairs of flip-flops (such as 51 and 52), in the arrangement shown in FIG. 16, for example, to provide separate output indications of positive and negative defects, and if desired, to provide operation of different conveyor diverting gates depending upon the type of defect detected. Operation of the system of FIG. 16 will be obvious in view of the preceding description.

In the modification partially illustrated in FIG. 19, the reject signals, which may comprise those from gate G2 in FIG. 3a, for example, are applied to a shift register SR2, which is assumed to have 100 stages. Pulses are applied to the shift input line of register SR2 from clock oscillator CS at a repetition rate which is 99 times the horizontal sweep repetition rate, or 1559.25 kilohertz. Thus a reject signal which occurs at a given point along a first scan line and is applied to the input line of the shift register will be shifted to stage 99 of the shift register by the time the same relative point is reached along the next scan line. The output line from stage 99 of the shift register is connected through inverter I99 and gate G90 to gate G91, which also receives the output signal from gate G2. Thus if a defect occurs at the same relative point along two successive scan lines, gate G91 will be enabled, providing a logic 1 output signal from inverter I101. If a defect instead occurs very slightly earlier along the second scan line, the pulse which was registered from the first line will have been shifted a slightly lesser distance along the shift register to stage 98 at the time the defect in the second line is detected, so that the inverted output from register output stage 98 will instead disable gate G90. If the defect occurs very slightly later along the second scan line, the pulse which was registered from the second line will have been shifted a slightly greater distance along the shift register to stage 100, so that the inverted output from register stage 100 will instead gate G90. If a defect occurs substantially earlier along the second line, or substantially later along the second line, than where it occurred along the first line, the pulse from detection of the defect during the first line will not have been shifted as far as stage 98, or will have been shifted past stage 100 out of the register at the time the defect along the second line is detected, so that gate G90 will remain enabled, and no logic 1 output signal will be provided by inverter I101. Thus it will be seen that a logic 1 defect-indicating signal will be provided from inverter I101 only if defects are detected on two successive lines at points along those two lines which either correspond or are not separated by more than a predetermined distance. The output line from inverter I101 may be connected to main detection gate G12 in lieu of the G2 input to G12 shown in FIG. 3a. Those skilled in the art will recognize that a delay line may be substituted for the shift register.

The principles of FIG. 19 may be extended in straightforward manner to provide indications of only defects which occur at substantially corresponding points along three (or more) successive scan lines, by extending the capacity of the shift register and adding similar gate connections from the extended portion. For example, a gate could be enabled only when a defect pulse from gate G2 is accompanied by a prior defect pulse then shifted to stage 99 or a stage closely adjacent thereto, and a further prior defect pulse then shifted to stage 198 or a stage closely adjacent thereto.

In FIG. 2a, wherein the x-rays are assumed to be directed downwardly, it will be seen that if a foreign particle were to lie at point F, closely adjacent the inside wall of the glass, it might or might not escape detection, depending upon what width one selected as the left sidewall of the jar in which defect detection is to be ignored. In applications where it is deemed vitally important that foreign particles lying close to the inside wall of a jar be detected, an arrangement of the nature of that shown in FIG. 17 may be employed. In FIG. 17 two x-ray sources are shown arranged to direct radiation at jar J along two distinctly different axes, which are shown 90° apart, by way of example. As the jar passes through the inspection zone, source 12a is energized for a first brief period and then source 12b is energized for a second similar period. They can be energized simultaneously if their directions are sufficiently different. The radiation from source 12a which passes through jar J impinges on an intensifier 15b which is viewed by camera 16a, while the radiation from source 12b which passes through the jar impinges on intensifier 15c which is viewed by camera 16b. The video signal from camera 16a is applied to a detection circuit such as that of FIGS. 3a and 3b for one inspection scanning field by camera and then the video signal from camera 16b is applied to the detection circuit for a similar inspection scanning field. It will be seen that although foreign particles at $f_1$ and $f_2$ lie closely adjacent the areas which intensifier 15b and camera 16a view as the sidewalls of the jar, so that they could be overlooked as the video from camera 16a is processed, they lie well away from the areas which intensifier 15c and camera 16b view as the sidewalls, so that they may be easily detected by processing the camera 16b video signals. Conversely, foreign particles at $f_3$ and $f_4$ might be overlooked as the camera 16b video is processed, but would be readily detected as the camera 16a video is processed. Particles adjacent the inside wall of the jar anywhere in between the four particles shown in FIG. 17 likely would be detected both as the camera 16a video is processed and as the camera 16b video is processed.

Arranging the radiation directions of the two sources at 90° tends to maximize the capability of the system to detect particles lying close to the wall of the jar, at the expense of requiring two separate image intensifiers and cameras with attendant camera switching. If the angle shown as 90° in FIG. 17 is reduced sufficiently, it will be seen that the radiation from both sources may be arranged to fall on a single intensifier having an adequate-size viewing field, and the image provided by that intensifier may be viewed by a single television camera.

In the inspection of certain articles, the detection of particles lying closely adjacent a container wall can instead be accomplished more simply by merely mechanically rotating the article in between two successive x-ray exposures. In FIG. 17a and 17b conveyor 10 is assumed to more jars rightwardly at a selected speed. A portion of the conveyor belt or floor 10e is provided with a slight tilt, with its edge 10a slightly lower than its edge 10b, as shown in FIG. 17b, so that bottom portions of the jars rub against stationary guide rail 9. Guide rail 9 is provided with a friction surface 9a such as a rubber strip. It will be seen that the tangential frictional force will rotate each jar as the conveyor moves the jars along the strip. Two (or more) x-ray exposures are made as the jar is rotated to two (or more) positions.

It should be understood that in the inspection of certain shaped articles, a camera scanning pattern other than a conventional television raster scan (successive parallel lines) may be used. In FIG. 18a an image of a doughnut is shown together with a few scan lines of a radial scanning pattern, wherein successive scan lines progress outwardly at different angles from a common center. The radial lines are shown with an exaggerated separation solely for sake of clarity. Modification of a television camera to incorporate radial scanning is well within the skill of the art, such scanning patterns having been used for many years in PPI radar scopes. The video from the successive radial scan lines may be processed in the manner previously shown for parallel scan lines. It will be apparent that the system resolution is greater near the center and decreases as a scan line progresses radially outwardly. Various applications also conceivably might utilize a circular scanning pattern of the nature shown in FIG. 18b, wherein each circle shown comprises a separate scan at a different radius, only a few of such lines being shown. If each circular scan line begins at a point in the same direction from the common center of the circular scan lines, such as at the radial line in FIG. 18b, and if each scan line has the same angular velocity about the center, it will be seen that successive circular scan lines may be compared with prior such lines in the same manner that parallel scan lines may be compared. Furthermore, while FIG. 18b diagrammatically indicates a step change in diameter between successive circular scan lines, it should now be apparent that the diameter may increase gradually as the scanning spot orbits around the center, i.e. a truly spiral scan may be used, assuming, of course, it, like the circular scans, provides constant angular velocity about the center. Successive circular scans may have either increasing or decreasing diameter, and a spiral scanning field may spiral either outwardly from the center or inwardly toward the center.

It is important to note that a wide variety of changes may be made in the logic circuits shown without departing from the invention. Different types of logic circuits may be substituted for those types shown in accordance with well known techniques, such as straight-forward manipulation of boolean expressions characteristic of the systems disclosed.

While a particular type of television camera has been suggested above as being suitable for use as camera 16 in FIG. 1, it is important to note that other well-known forms of television camera may instead by used, such as a vidicon, a plumbicon, or an image orthicon, each of which will integrate received light as a radiographic image is presented on an intensifier screen or the like and store a pattern of charges characteristic of the image which will remain after cessation of the x-ray pulse removes the image from the screen until the pattern is scanned, which tends to discharge or erase the pattern of charges. Various known forms of self-scanning photosensor arrays of the "Reticon" type may be used. Furthermore, various types of image intensifiers may be used, including x-ray image intensifiers of both tube and solid-state versions, and optical image intensifiers, and for some applications use of an image intensifier per se may be deemed unnecessary. For example, in some applications if sufficient x-ray energy is provided, a radiographic image appearing on an x-ray fluorescent screen may be viewed directly (through a lens system or its equivalent) by a television camera. In its broadest sense the invention may use as an input conversion means any device or series of devices which perform the function of receiving x-ray radiation passed through an article and providing therefrom an optical (i.e. focusable) image which may be scanned to provide a video signal, with the term optical not being restricted to a visible image, but also embracing ultraviolet, infra-red and electron optical images.

While the system has been described in connection with the inspection of products contained within cylindrical glass jars, it will be apparent at this point that the invention is applicable as well to the inspection of products in glass bottles or jars which may have a generally rectangular shape, and in various other types of containers, such as plastic or paper containers, and aluminum and other metal cans, which may have a cylindrical or rectangular shape, and indeed, numerous features of the invention are readily applicable to the inspection of articles which are not carried in containers per se. While the system has been described in connection with the inspection of jars carried erect on a conveyor, it will be apparent that the system disclosed may readily be adapted to the inspection of jars or the like carried on their sides, by mere rotation of the scanning field direction.

It will thus be seen that the objects set forth above, among those made apparent from the preceding description, are efficiently attained. Since certain changes may be made in carrying out the above method and in the constructions set forth without departing from the scope of the invention, it is intended that all matter contained in the above description or shown in the accompanying drawings shall be interpreted as illustrative and not in a limiting sense.

It is also to be understood that the following claims are intended to cover all the generic and specific features of the invention herein described, and all statements of the scope of the invention which, as a matter of language, might be said to fall therebetween.

The embodiments of the invention in which an exclusive property or privilege is claimed are defined as follows:

1. X-ray inspection apparatus, comprising, in combination: first means for irradiating an article to be inspected with x-ray radiation to derive an optical image having a brightness variation characteristic of the radiation absorption of said article; means for scanning said optical image with a plurality of successive scan lines to derive a respective plurality of line scan signals; means for comparing each of said line scan signals with at least one prior one of said line scan signals of said plurality to detect differences between said signals; and means for providing a reject indication signal if the magnitudes of a predetermined number of said differences exceed a tolerance value.

2. Apparatus according to claim 1 wherein said first means comprises radiation source means, means for energizing said radiation source means during a first time interval, and radiation-sensitive image intensifier means disposed to receive radiation passed through said article during said first time interval and operative to provide said optical image, and wherein said means for scanning comprises television camera means operative to receive an image charge from said intensifier means during said first time interval, and operative to scan said image charge within a second time interval beginning after the end of said first time interval to derive said line scan signals.

3. Apparatus according to claim 1 having delay means connected between said means for scanning and said means for comparing for delaying the application of each of said line scan signals to said means for comparing by a predetermined amount.

4. Apparatus according to claim 1 wherein said means for comparing comprises difference detector means operable to provide output signals commensurate with the magnitudes and signs of the differences between each of said line scan signals and said at least one prior line scan signal; and wherein said means for providing said reject indication signal comprises first comparator means connected to receive said output signals from said difference detector means and a first reference signal and operative to provide an output signal whenever said output signals from said difference detector means exceeds said first reference signal, second comparator means connected to receive said output signals from said difference detector means and a second reference signal and operative to provide an output signal whenever said output signals from said difference detector means are less than said second reference signal, and means responsive to the output signals from said first and second comparator means for providing a reject indication signal.

5. Apparatus according to claim 1 wherein said means for providing a reject indication signal includes means responsive to said plurality of line scan signals for providing an enabling signal upon detecting the first of said line scan signals of said plurality of which a selected portion does not cross a predetermined threshold value, and means responsive to said enabling signal for providing said reject indication signal if the magnitude of one or more of said differences exceeds a predetermined tolerance value as said means for comparing compares successive ones of said line scan signals occurring after said first of said line scan signals.

6. Apparatus according to claim 1 wherein said apparatus includes sensing means operable upon sensing the presence of said article to actuate said first means during a first time interval and thereafter to actuate said means for scanning during a second time interval.

7. Apparatus according to claim 1 wherein said means for comparing includes first delay means for delaying each of said line scan signals with a first time delay less than the period of each of said line scan signals to provide a first plurality of delayed line scan signals, second delay means for delaying each of said delayed line scan signals with a second time delay equal to the period of each of said line scan signals to provide a second plurality of delayed line scan signals, and comparator means for comparing each of said delayed line scan signals of said first plurality with a respective delayed line scan signal of said second plurality.

8. Apparatus according to claim 1 wherein said predetermined number in one.

9. Apparatus according to claim 1 wherein the last-recited means is operative to provide said reject indication only if the magnitudes of said predetermined number of said differences exceed said tolerance value at times during an uninterrupted sequence of a predetermined number of said line scan signals.

10. Apparatus according to claim 1 having means for gradually varying said tolerance value as successive ones of said line scan signals are compared by said means for comparing.

11. Apparatus according to claim 1 wherein the last-recited means includes means for varying said tolerance value during a selected portion of at least one of said scan lines.

12. Apparatus according to claim 1 having video monitor means responsive to said line scan signals and operative to provide a visible image of said article; and means responsive to said reject indication signal for varying at least one of the line scan signals applied to said video monitor means to provide an indicium in said visible image indicating the presence of a defect.

13. Apparatus according to claim 1 in which said means for scanning is operative to scan said image with a plurality of mutually parallel scan lines.

14. Apparatus according to claim 1 in which said means for scanning is operative to scan said image with a plurality of successive circular scan lines each progressing at the same angular velocity around a common central point.

15. Apparatus according to claim 1 in which said means for scanning is operative to scan said image with a plurality of successive scan lines each of which comprises a one-revolution portion of a spiral about a central point and each of which progresses at the same angular velocity about said central point.

16. Apparatus according to claim 1 in which said means for scanning is operative to scan said image along a plurality of successive scan lines which progress in mutually different directions and intersect at a common central point.

17. Apparatus according to claim 1 wherein said means for comparing is operative to provide output signals commensurate with said differences between said signals; and said means for providing a reject indication signal comprises a plurality of comparator means each responsive to said output signals from said means for comparing and each responsive to a respective reference signal, and a plurality of storage means, each of said storage means being operably responsive to output signals from a respective one of said comparator means.

18. Apparatus according to claim 1 wherein said means for comparing comprises means for amplifying each of said line scan signals substantially logarithmically.

19. Apparatus according to claim 1 which includes means responsive to each of said line scan signals for providing a logic signal whenever the magnitude of said line scan signals for providing a logic signal whenever the magnitude of a line scan signal lies below a first level, said means for providing a reject indication signal includes gating circuit means responsive to said logic signal and enabled to provide said reject indication signal a predetermined time after the occurrence of said logic signal, and means for varying said tolerance value for a predetermined time after said gating circuit means is enabled.

20. Apparatus according to claim 1 in which said means for comparing includes delay means having a delay period commensurate with the period of each of said line scan signals.

21. Apparatus according to claim 20 in which said means for comparing includes adder means connected to simultaneously receive a given one of said line scan signals and a feedback signal commensurate with line scan signals prior to said given one of said line scan signals and operative to combine said given one of said line scan signals and said feedback signal to provide a further signal, said further signal being connected to be applied to said delay means.

22. Apparatus according to claim 21 wherein said means for deriving said enabling signals comprises means responsive to each of said line scan signals for providing a predetermined logic signal whenever the magnitude of a line scan signal exceeds a first level, and means responsive to said logic signal and to said first enabling signal for providing a second enabling signal of said plurality of enabling signals.

23. Apparatus according to claim 22 wherein said means responsive to said logic signal is operative to respond to said logic signal with a predetermined delay.

24. Apparatus according to claim 22 having means for varying said predetermined delay to different values while at least two different ones of said scan lines are scanned.

25. Apparatus according to claim 1 having means for varying said tolerance value as successive groups of said line scan signals are compared by said means for comparing.

26. Apparatus according to claim 25 having means for modifying said successive groups of line scan signals to provide successive groups of modified line scan signals; and video monitor means operative in response to said modified line scan signals for providing a visible image of said article having indicia representing the variation of said tolerance value.

27. Apparatus according to claim 1 wherein said means for providing a reject indication signal comprises comparator means for providing respective first signals when the magnitudes of said differences exceed said predetermined tolerance value, a coincidence circuit means responsive to simultaneous receipt of each of said first signals and a plurality of enabling signals to provide an output signal, and means for deriving and applying said plurality of enabling signals to said coincidence circuit means.

28. Apparatus according to claim 27 wherein said means for providing a reject indication includes first storage means operative to store said output signal from said coincidence means, second storage means for receiving and storing an output signal from said first storage means, and gate circuit means operative to transfer an output signal from said first storage means to said second storage means, said means for deriving said plurality of enabling signals includes means for applying a first enabling signal of predetermined duration to said coincidence circuit means during each of said successive scan lines, means responsive to each of said line scan signals for providing a predetermined logic signal whenever the magnitude of a line scan signal exceeds a first level, and means responsive to said logic signal and said first enabling signal for actuating said circuit means.

29. Apparatus according to claim 28 wherein said means responsive to said logic signal is operative to respond to said logic signal with a predetermined delay.

30. Apparatus according to claim 27 wherein said means for deriving said plurality of enabling signals comprises means for applying a first enabling signal of predetermined duration during each of said successive scan lines.

31. Apparatus according to claim 30 wherein said means for deriving said enabling signals comprises means responsive to each of said line scan signals for providing a predetermined logic signal whenever the magnitude of a line scan signal lies below a first level, and means responsive to said logic signal and to said first enabling signal for providing a second enabling signal of said plurality of enabling signals.

32. Apparatus according to claim 31 wherein said means responsive to said logic signal is operative to respond to termination of said logic signal with a predetermined delay.

33. Apparatus according to claim 1 wherein said means for providing a reject indication signal comprises first comparator means for providing an output signal if one of said differences exceeds a first tolerance value in one direction and second comparator means for providing an output signal if one of said differences exceeds a second tolerance value in the opposite direction.

34. Apparatus according to claim 33 wherein said second tolerance value differs from said first tolerance value.

35. Apparatus according to claim 33 wherein said apparatus includes means for disabling one of said comparator means during the occurrence of a selected group of said successive scan lines.

36. Apparatus according to claim 1 which includes detecting means responsive to said plurality of line scan signals for detecting whether a selected portion of any of said line scan signals crosses a predetermined threshold value; and means responsive to said detecting means for providing an output signal if none of said selected portions of a predetermined number of said line scan signals crosses said predetermined threshold value.

37. Apparatus according to claim 36 which includes conveyor means for transporting successive articles past an inspection zone, motive means for driving said conveyor means, and means responsive to said output signal for stopping said motive means to halt said conveyor means.

38. Apparatus according to claim 1 wherein said means for providing said reject indication signal comprises comparator means operative to provide an output signal whenever the magnitude of one of said differences between said signals exceeds said tolerance value during the comparison of each of said line scan signals, delay means connected to receive the output signals from said comparator means, and coincidence circuit means responsive to said output signals from said comparator means and output signals from said delay means and operative to provide an output signal.

39. Apparatus according to claim 38 wherein said delay means comprises a shift register connected to be shifted at a repetition rate which is a multiple of the rate at which said successive scan lines are scanned, and said coincidence circuit means are connected to receive signals from selected stages of said shift register to provide an output signal only if said comparator means provides output signals during the comparison of a successive plurality of said line scan signals at times which do not vary by more than a predetermined amount from the period of each of said scan lines.

40. Apparatus according to claim 1 wherein said first means comprises an x-ray tube, presence sensor means for sensing the arrival of said article to be inspected at an inspection zone for providing a first signal having a time duration less than one cycle of said voltage source, means responsive to said first signal and to an alternating voltage source for providing a second signal during the first half-cycle of said voltage source following the occurrence of said first signal, and wherein said means for scanning comprises television camera means connected to be blanked by said second signal.

41. Apparatus according to claim 40 having pulser means operable upon occurrence of said second signal for connecting said x-ray tube to said voltage source for a predetermined time.

42. Apparatus according to claim 41 having means for varying said predetermined delay to different values while at least two different ones of said scan lines are scanned.

43. The method of inspecting an article within a container to sense the presence of defects in said article while ignoring predetermined edge portions of said container, comprising the steps of irradiating said article and container to provide an image containing a representation of said article and container within a background area; scanning said image with at least one scan line which crosses said representation of said article and container and portions of said background area on opposite sides of said representation to derive a time-varying scan line signal; sensing a transition of said scan line signal as said scan line passes from said representation to a portion of said background area on one side of said representation to provide a timing signal; delaying said scan line signal with a predetermined delay; and comparing the delayed scan line signal with a prior scan line signal for a predetermined amount of time after the occurrence of said timing signal to detect one or more differences between said delayed scan line signal and said prior scan line signal.

44. In inspection apparatus for detecting defects in products contained within containers and ignoring desired side wall portions of said containers, which apparatus includes means for providing an image which includes representations of said side wall portions of a container and product within a container situated in a background area, means for scanning said image and background area with a plurality of successive scan lines to derive a succession of respective video line scan signals, processing means for receiving and processing said video line scan signals to detect defects in said product, and storage means for storing signals indicating defects, the combination of: logic means responsive to said video line scan signals for conditionally enabling said storage means during each of said scan lines a first predetermined amount of time after a scan line passes from said background area into a portion of said image representing one of said side wall portions of said container and for disabling said storage means during each of said scan lines at a second predetermined amount of time after a scan line passes from a product portion of said image to a side wall portion of said image; and delay means for delaying the passage of each of said video line scan signals to said processing means with a predetermined amount of delay, whereby said storage means is conditionally enabled only while portions of the delayed video line scan signals representing product located between said side wall portions of said image are being processed by said processing means.

45. The combination according to claim 44 which includes means for disabling said storage means during each of said successive lines until the scanning of a line following the first of said lines in which a selected portion of the video signal did not cross a predetermined threshold value.

46. The combination according to claim 44 wherein said processing means comprises means for comparing each of said line scan signals with at least one line scan signal derived from a prior scan line to detect each difference in amplitude between the signals being compared which exceeds a selected magnitude.

47. The combination according to claim 44 having video monitor means responsive to said video line scan signals and operable to provide a visible display of said article; and means responsive to said logic means for varying the video line scan signals applied to said monitor means as said storage means is conditionally enabled and disabled to provide indicia in said display indicating an area in which the detection of a defect will result in storage of a defect-indicating signal in said storage means.

48. The method of inspecting an article which comprises the steps of: irradiating said article with x-ray radiation to provide an image thereof; scanning said image with a plurality of successive scan lines comprising a scanning field to derive a respective plurality of line scan signals, each of said line scan signals comprising a time-varying waveform characteristic of the variation in brightness of said image along a respective one of said scan lines; successively delaying and combining said line scan signals to provide a plurality of successive delayed line scan signals; comparing each of said line scan signals with a respective one of said delayed line scan signals to provide further signals commensurate with differences therebetween; and providing a rejection signal if the magnitude of one or more of said further signals exceeds a predetermined value.

49. The method of claim 48 wherein said step of successively delaying and combining said line scan signals comprises combining each successive line scan signal with signals emanating from a delay device to provide summed signals, and applying said summed signals to said delay device.

50. X-ray inspection apparatus, comprising, in combination: means for irradiating an article to be inspected with x-ray radiation during a first time interval; radiation-sensitive image intensifier means disposed to receive radiation passed through said article during said first time interval and operative to provide an optical image of said article during said time interval; television camera means disposed to receive said optical image during said first time interval and operative to begin to provide video signals during a second time interval beginning after the end of said first time interval, said camera means including target means having storage elements adapted to be charged by said optical image during said first time interval and scanning means for scanning said storage elements of said target means during said second time interval to provide said video signals; and video signal-processing means for processing said video signals to provide at least one output signal characteristic of said article.

51. X-ray inspection apparatus, comprising, in combination: first means for irradiating an article to be inspected with x-ray radiation to derive an optical image having a brightness variation characteristic of the radiation absorption and said article; means for scanning said optical image to derive a plurality of line scan signals each commensurate with said brightness variation along a respective scan line across said image; means for comparing each of said line scan signals representing said brightness variation along a respective given line across said image with at least another of said line scan signals representing said brightness variation along a line adjacent to said given line to detect instantaneous amplitude differences therebetween; and means for providing a reject indication signal if the magnitude of a predetermined number of said differences exceeds a tolerance value.

* * * * *